US011691135B2

United States Patent
El Ali et al.

(10) Patent No.: US 11,691,135 B2
(45) Date of Patent: Jul. 4, 2023

(54) SYNTHESIS OF ALKYNONES VIA CARBONYLATIVE SONOGASHIRA COUPLING REACTIONS CATALYZED BY PD(II)-N-HETEROCYCLIC CARBENE-PYRIDINE COMPLEXES

(71) Applicants: King Fahd University of Petroleum & Minerals, Dhahran (SA); Saudi Arabian Oil Company, Dhahran (SA)

(72) Inventors: Bassam El Ali, Dhahran (SA); Waseem Mansour, Dhahran (SA); Mohammed Fettouhi, Dhahran (SA)

(73) Assignees: King Fahd University of Petroleum & Minerals, Dhahran (SA); Saudi Arabian Oil Company, Dhahran (SA)

( * ) Notice: Subject to any disclaimer, the term of this patent is extended or adjusted under 35 U.S.C. 154(b) by 330 days.

(21) Appl. No.: 17/071,713

(22) Filed: Oct. 15, 2020

(65) Prior Publication Data

US 2022/0118435 A1 Apr. 21, 2022

(51) Int. Cl.
| | |
|---|---|
| *C07C 45/49* | (2006.01) |
| *C07C 201/12* | (2006.01) |
| *C07D 307/58* | (2006.01) |
| *C07F 15/06* | (2006.01) |
| *B01J 31/22* | (2006.01) |
| *C07C 45/50* | (2006.01) |
| *C07F 15/00* | (2006.01) |

(52) U.S. Cl.
CPC .......... *B01J 31/2273* (2013.01); *C07C 45/50* (2013.01); *C07C 201/12* (2013.01); *C07D 307/58* (2013.01); *C07F 15/006* (2013.01); *B01J 2231/321* (2013.01); *C07C 2601/14* (2017.05)

(58) Field of Classification Search
CPC ..... C07C 45/49; C07C 201/12; C07D 307/58; C07F 15/006
See application file for complete search history.

(56) References Cited

U.S. PATENT DOCUMENTS

| | | |
|---|---|---|
| 2007/0073055 A1 | 3/2007 | Organ et al. |
| 2009/0326237 A1 | 12/2009 | Strassner et al. |
| 2019/0016741 A1 | 1/2019 | Hollis et al. |
| 2019/0374933 A1 | 12/2019 | Nolan |
| 2022/0119433 A1 | 4/2022 | El Ali et al. |

FOREIGN PATENT DOCUMENTS

| | | |
|---|---|---|
| CN | 109810147 | 5/2019 |

OTHER PUBLICATIONS

U.S. Appl. No. 17/071,381, filed Oct. 15, 2020, Ali et al.
U.S. Appl. No. 17/094,140, filed Nov. 10, 2020, Ali et al.
Avery et al., "Use of a silicon carbide multi-well plate in conjunction with microwave heating for rapid ligand synthesis, formation of palladium complexes, and catalyst screening in a Suzuki coupling," Tetrahedron Letters 50.24, 2009, 2851-2853, 3 pages.
Awuah et al., Access to Flavones via a Microwave-Assisted, One-Pot Sonogashira-Carbonylation-Annulation Reaction Org. Lett. vol. 11, 2009, 3210-3213, 4 pages.
Babu et al., "Synthesis and biological evaluation of novel 8-aminomethylated oroxylin A analogues as alpha-glucosidase inhibitors." Bioorganic & medicinal chemistry letters 18.5, 2008, 1659-1662, 4 pages.
Baruah et al., "Ru (ii)-Catalyzed C—H activation and annulation of salicylaldehydes with monosubstituted and disubstituted alkynes." Chemical Communications 52.88, 2016, 13004-13007, 4 pages.
Boncel et al., "Michael-type addition of azoles of broad-scale acidity to methyl acrylate." Beilstein journal of organic chemistry 7.1, 2011, 173-178, 6 pages.
Brimble et al., "Pyrans and their Benzo Derivatives: Synthesis." Comprehensive Heterocyclic Chemistry III, 2008, 281 pages.
Chinchilla et al., "The Sonogashira reaction: a booming methodology in synthetic organic chemistry," Chemical reviews 107.3, 2007, 874-922.
Demirayak et al., "New chroman-4-one/thiochroman-4-one derivatives as potential anticancer agents." Saudi Pharmaceutical Journal 25.7,2017, 1063-1072, 31 pages.
Ferreira et al., "Flavonoid compounds as reversal agents of the P-glycoprotein-mediated multidrug resistance: biology, chemistry and pharmacology." Phytochemistry Reviews 14.2, 2015, 233-272, 40 pages.
Gazvoda et al., "A mesoionic bis (Py-tz NHC) palladium (ii) complex catalyses "green" Sonogashira reaction through an unprecedented mechanism." Chemical Communications 52.8, 2016, 1571-1574, 4 pages.
Hahn et al., "The Pd (II) complex of a bidentate di (benzimidazol-2-ylidene) ligand." Zeitschrift für Naturforschung B 59.5, 2004, 541-543, 3 pages.
Hao et al., "The first heterogeneous carbonylative Sonogashira coupling reaction catalyzed by MCM-41-supported bidentate phosphine palladium (0) complex." Journal of Molecular Catalysis A: Chemical 298.1-2, 2009, 94-98, 5 pages.
Harvey et al., "A new chromone and flavone synthesis and its utilization for the synthesis of potentially antitumorigenic polycyclic chromones and flavones." The Journal of Organic Chemistry 55.25, 1990, 6161-6166, 6 pages.
Hostetler et al., "Flavones: Food sources, bioavailability, metabolism, and bioactivity." Advances in Nutrition 8.3, 2017, 423-435, 13 pages.
Islam et al., "Potent a-glucosidase and protein tyrosine phosphatase 1B inhibitors from Artemisia capillaris." Archives of pharmacal research 36.5, 2013, 542-552, 11 pages.
Ismail et al., "Synthesis and biological evaluation of some novel 4H-benzopyran-4-one derivatives as nonsteroidal antiestrogens." European journal of medicinal chemistry 36.3, 2001, 243-253, 11 pages.
Jagadeesan et al., "The nature of Pd-carbene and Pd-halogen bonds in (bisNHC) PdX 2 type catalysts: insights from density functional theory," RSC advances 5.98, 2015, 80661-80667, 7 pages.

(Continued)

*Primary Examiner* — Sikarl A Witherspoon
(74) *Attorney, Agent, or Firm* — Fish & Richardson P.C.

(57) ABSTRACT

This disclosure relates to N-substituted Pd(II)-N-heterocyclic carbene-pyridine complexes, methods of preparing the complexes, and methods of using the complexes in Sonogashira coupling reactions.

30 Claims, No Drawings

(56) References Cited

OTHER PUBLICATIONS

Kabalka et al., "Microwave-assisted synthesis of functionalized flavones and chromones." Tetrahedron Letters 46.37, 2005, 6315-6317, 3 pages.
Keri et al., "Chromones as a privileged scaffold in drug discovery: A review." European journal of medicinal chemistry 78, 2014, 340-374, 35 pages.
Kim et al., "Unified approach to (thio) chromenones via one-pot Friedel-Crafts acylation/cyclization: Distinctive mechanistic pathways of β-chlorovinyl ketones." Organic letters 19.2, 2017, 312-315, 4 pages.
Liu et al., "Construction of the flavones and aurones through regioselective carbonylative annulation of 2-bromophenols and terminal alkynes." Tetrahedron Letters 54.14, 2013, 1802-1807, 6 pages.
Maiti et al., "Synthesis and cancer chemopreventive activity of zapotin, a natural product from Casimiroa edulis." Journal of medicinal chemistry 50.2, 2007, 350-355, 6 pages.
Mansour et al., "Novel and efficient bridged bis (N-heterocyclic carbene) palladium (II) catalysts for selective carbonylative Suzuki-Miyaura coupling reactions to biaryl ketones and biaryl diketones." Applied Organometallic Chemistiy 34.6, e5636, 2020, 20 pages.
Miao et al., "Regiospecific carbonylative annulation of iodophenol acetates and acetylenes to construct the flavones by a new catalyst of palladium-thiourea-dppp complex." Organic letters 2.12, 2000, 1765-1768, 4 pages.
Mohapatra et al., "Michael Addition of Imidazole to α, β-Unsaturated Carbonyl/Cyano Compound." Open Chemistry Journal 5.1, 2018, 14 pages.
Morimoto et al., "Insect antifeedant activity of flavones and chromones against Spodoptera litura." Journal of agricultural and food chemistry 51.2, 2003, 389-393, 5 pages.
Muskawar et al., "NHC-metal complexes based on benzimidazolium moiety for chemical transformation: 1st Cancer Update." Arabian Journal of Chemistry 9, 2016, S1765-S1778, 14 pages.
Musthafa et al., "Microwave-assisted solvent-free synthesis of biologically active novel heterocycles from 3-formylchromones." Medicinal Chemistry Research 20.9, 2011,1473-1481, 9 pages.
Netzer et al., "The actual role of sodium cromoglycate in the treatment of asthma—a critical review." Sleep and Breathing 16.4, 1027-1032, 2012, 6 pages.
Qi et al., "Selective palladium-catalyzed carbonylative synthesis of aurones with formic acid as the CO source." RSC advances 6.67,2016, 62810-62813, 4 pages.
Rueping et al., "A review of new developments in the Friedel-Crafts alkylation—From green chemistry to asymmetric catalysis." Beilstein journal of organic chemistry 6.1, 2010, 24 pages.
Sartori et al., Advances in Friedel-Crafts Acy/ation Reactions: Catalytic and Green Processes book 1st Edition, 2009, 222 pages.
Taniguchi, "Aerobic nickel-catalyzed hydroxysulfonylation of alkenes using sodium sulfinates." The Journal of organic chemistry 80.15, 2015, 7797-7802, 20 pages.
Wu et al., "Palladium-Catalyzed Carbonylation Reaction of Aryl Bromides with 2-Hydroxyacetophenones to Form Flavones." Chemistry—A European Journal 18.40, 2012, 12595-12598, 5 pages.
Xu et al., "Divergent synthesis of flavones and aurones via base-controlled regioselective palladium catalyzed carbonylative cyclization," Molecular Catalysis 452, 2018, 264-270, 7 pages.
Xue et al., "Pd-carbene catalyzed carbonylation reactions of aryl iodides." Dalton Transactions 40.29, 2011, 7632-7638, 7 pages.
Yang et al., "Pd catalyzed couplings of "superactive esters" and terminal alkynes: Application to flavones and γ-benzopyranones construction." Journal of Molecular Catalysis A: Chemical 426, 2017, 24-29, 6 pages.
Yang et al., "Synthesis of chromones via palladium-catalyzed ligand-free cyclocarbonylation of o-iodophenols with terminal acetylenes in phosphonium salt ionic liquids." The Journal of organic chemistiy 75.3, 2010, 948-950, 3 pages.
Yaşar et al., "Microwave-Assisted Synthesis of 4'-Azaflavones and Their N-Alkyl Derivatives with Biological Activities." Chemistry & biodiversity 5.5, 2008, 830-838, 9 pages.
Yoshida et al., "A concise total synthesis of biologically active frutinones via tributylphosphine-catalyzed tandem acyl transfer-cyclization," Tetrahedron 70.21, 2014, 3452-3458, 7 pages.
Zhang et al., "Enantioselective formal [4+2] annulation of ortho-quinone methides with orthohydroxyphenyl α, β-unsaturated compounds." The Journal of organic chemistry 83.17, 2018, 10175-10185, 11 pages.
Zhao et al., "C-H functionalization via remote hydride elimination: Palladium catalyzed dehydrogenation of ortho-acyl phenols to flavonoids." Organic letters 19.5, 2017, 976-979, 4 pages.
Zhao et al., "Synthesis and insecticidal activity of chromanone and chromone analogues of diacylhydrazines." Bioorganic & medicinal chemistry 15.5, 2007, 1888-1895, 8 pages.
Zhiping et al., "Transition-Metal-Catalyzed Carbonylative Synthesis and Functionalization of Heterocycles." Chinese Journal of Organic Chemistry 39.3, 2019, 573-590, 18 pages.
Zhong et al., "An efficient synthesis of 4-chromanones." Tetrahedron letters 52.38, 2011, 4824-4826, 3 pages.
Zhou et al., "Synthesis of indoles through Palladium-catalyzed three-component reaction of aryl iodides, alkynes, and diaziridinone." Organic letters 20.20, 2018, 6440-6443, 4 pages.
Zhu et al., "Highly efficient synthesis of flavones via Pd/C-catalyzed cyclocarbonylation of 2-iodophenol with terminal acetylenes." Catalysis Science & Technology 6.9, 2016, 2905-2909, 4 pages.
Aktaş et al., "Mixed phosphine/N-heterocyclic carbene-palladium complexes: synthesis, characterization, crystal structure and application in the Sonogashira reaction in aqueous media." Transition Metal Chemistry 44.3, 2019, 229-236, 8 pages.
Aktaş et al., "Novel morpholine liganded Pd-based N-heterocyclic carbene complexes: Synthesis, characterization, crystal structure, antidiabetic and anticholinergic properties." Polyhedron 159, 2019, 345-354, 32 pages.
Bai, Cuihua, et al. "Carbonylative Sonogashira coupling of terminal alkynes with aryl iodides under atmospheric pressure of CO using Pd (II) MOF as the catalyst." Catalysis Science & Technology 4.9, 2014, 3261-3267, 7 pages.
Brennführer et al., "Palladium-catalyzed carbonylation reactions of aryl halides and related compounds." Angewandte Chemie International Edition 48.23, 2009, 4114-4133, 20 pages.
Cui et al., "Carbonylative Suzuki coupling reactions of aryl iodides with arylboronic acids over Pd/SiC." Chinese Journal of Catalysis 36.3, 2015, 322-327, 6 pages.
Feng et al., "Carbonylative Sonogashira Coupling of Aryl Iodides with Terminal Alkynes Catalyzed by Palladium Nanoparticles." Journal of the Chinese Chemical Society 65.3, 2018, 337-345.
Gadge et al., "Recent developments in palladium catalysed carbonylation reactions." RSC Advances 4.20, 2014, 10367-10389, 23 pages.
Gautam et al., "Aminophosphine Palladium Pincer-Catalyzed Carbonylative Sonogashira and Suzuki-Miyaura Cross-Coupling with High Catalytic Turnovers." ACS omega 4.1, 2019, 1560-1574, 15 pages.
Gautam et al., "Palladacycle-Catalyzed Carbonylative Suzuki-Miyaura Coupling with High Turnover Number and Turnover Frequency." The Journal of organic chemistry 80.15, 2015, 7810-7815, 19 pages.
Genelot et al., "Carbonylative Sonogashira coupling in the synthesis of ynones: a study of "boomerang" phenomena." Advanced Synthesis & Catalysis 355.13, 2013, 2604-2616, 14 pages.
He et al., "Highly enantioselective azadiene Diels-Alder reactions catalyzed by chiral N-heterocyclic carbenes." Journal of the American Chemical Society 128.26, 2006, 8418-8420, 3 pages.
Hopkinson et al., "An overview of N-heterocyclic carbenes." Nature 510.7506, 2014, 485-496, 12 pages.
Huynh et al., "Syntheses and catalytic activities of Pd (II) dicarbene and hetero-dicarbene complexes." Journal of Organometallic Chemistry 696.21, 2011, 3369-3375, 7 pages.
Ibrahim et al., "Efficient N-heterocyclic carbene palladium (II) catalysts for carbonylative Suzuki-Miyaura coupling reactions leading to aryl ketones and diketones." Journal of Organometallic Chemistry 859, 2018, 44-51, 21 pages.

(56) References Cited

OTHER PUBLICATIONS

Ibrahim et al., "Novel (N-heterocyclic carbene) Pd (pyridine) Br2 complexes for carbonylative Sonogashira coupling reactions: Catalytic efficiency and scope for arylalkynes, alkylalkynes and dialkynes." Applied Organometallic Chemistry 32.4, 4280, 2018, 1.

Ibrahim et al., "Synthesis, crystal structures and catalytic activities of new palladium (II)—bis (oxazoline) complexes." Transition Metal Chemistry 41.7, 2016, 739-749.

Ishiyama et al., "Synthesis of unsymmetrical biaryl ketones via palladium-catalyzed carbonylative cross-coupling reaction of arylboronic acids with iodoarenes." Tetrahedron letters 34.47, 1993, 7595-7598, 4 pages.

Kang et al., "Pd (0)-Cu (I)-catalyzed cross-coupling of alkynylsilanes with triarylantimony (V) diacetates." Journal of the Chemical Society, Perkin Transactions 1 7 (2001): 736-739, 4 pages.

Ketike et al., "Carbonylative Suzuki-Miyaura cross-coupling over Pd NPs/Rice-Husk carbon-silica solid catalyst: Effect of 1, 4-dioxane solvent." ChemistrySelect 3.25, 2018, 7164-7169, 6 pages.

Kobayash et al., "Carbonylation of organic halides in the presence of terminal acetylenes; novel acetylenic ketone synthesis." Journal of the Chemical Society, Chemical Communications 7, 1981, 333-334, 2 pages.

Kostyukovich et al., "In situ transformations of Pd/NHC complexes with N-heterocyclic carbene ligands of different nature into colloidal Pd nanoparticles." Inorganic Chemistry Frontiers 6.2, 2019, 482-492, 11 pages.

Kumar et al., "Stereoelectronic Profiling of Expanded-Ring N-Heterocyclic Carbenes." Inorganic chemistry 58.11, 2019, 7545-7553, 9 pages.

Lee et al., "Carbonylative Coupling of 4, 4'-Diiodobiphenyl Catalyzed by Pd (NHC) Complex.", 2013, 4 pages.

Liang et al., "Pd-catalyzed copper-free carbonylative Sonogashira reaction of aryl iodides with alkynes for the synthesis of alkynyl ketones and flavones by using water as a solvent." The Journal of organic chemistry 70.15, 2005, 6097-6100, 4 pages.

Liu et al., "Magnetically separable Pd catalyst for carbonylative sonogashira coupling reactions for the synthesis of α, β-alkynyl ketones." Organic letters 10.18, 2008, 3933-3936, 4 pages.

Ma et al., "N-Heterocyclic carbene-stabilized palladium complexes as organometallic catalysts for bioorthogonal cross-coupling reactions." The Journal of organic chemistry 79.18, 2014, 8652-8658, 7 pages.

Mingji, Dai, et al. "A novel thiourea ligand applied in the Pd-catalyzed Heck, Suzuki and Suzuki carbonylative reactions." Advanced Synthesis & Catalysis 346.13-15, 2004, 1669-1673, 5 pages.

Mohamed et al., "Carbonylative sonogashira coupling of terminal alkynes with aqueous ammonia." Organic letters 5.17 (2003): 3057-3060, 4 pages.

Nelson et al., "Quantifying and understanding the electronic properties of N-heterocyclic carbenes." Chemical Society Reviews 42.16, 2013, 6723-6753, 31 pages.

Nguyen et al., "Postmodification Approach to Charge-Tagged 1, 2, 4-Triazole-Derived NHC Palladium (II) Complexes and Their Applications." Organometallics 36.12, 2017, 2345-2353, 9 pages.

Niu, Jian-Rui, et al. "Preparation of Recoverable Pd Catalysts for Carbonylative Cross-Coupling and Hydrogenation Reactions." ChemCatChem 5.1 (2013): 349-354, 6 pages.

Niu, Jianrui, et al. "Stabilizing Pd II on hollow magnetic mesoporous spheres: a highly active and recyclable catalyst for carbonylative cross-coupling and Suzuki coupling reactions." New Journal of Chemistry 38.4, 2014, 1471-1476, 6 pages.

O'Keefe et al., "Carbonylative Cross-Coupling of ortho-Disubstituted Aryl Iodides. Convenient Synthesis of Sterically Hindered Aryl Ketones." Organic letters 10.22, 2008, 5301-5304, 4 pages.

Park et al., "Pd-catalyzed carbonylative reactions of aryl iodides and alkynyl carboxylic acids via decarboxylative couplings." Organic Letters 13.5, 2011, 944-947, 4 pages.

Rajabi et al., "An Efficient Palladium N-Heterocyclic Carbene Catalyst Allowing the Suzuki-Miyaura Cross-Coupling of Aryl Chlorides and Arylboronic Acids at Room Temperature in Aqueous Solution," Advanced Synthesis & Catalysis 356.8, 2014, 1873-1877, 5 pa.

Sakaguchi et al., "Chiral Palladium (II) Complexes Possessing a Tridentate N-Heterocyclic Carbene Amidate Alkoxide Ligand: Access to Oxygen-Bridging Dimer Structures." Angewandte Chemie International Edition 47.48, 2008, 9326-9329, 4 pages.

Schmid et al., "Mixed phosphine/N-heterocyclic carbene palladium complexes: Synthesis, characterization and catalytic use in aqueous Suzuki-Miyaura reactions." Dalton Transactions 42.20, 2013, 7345-7353, 9 pages.

Tambade et al., "Copper-Catalyzed, Palladium-Free Carbonylative Sonogashira Coupling Reaction of Aliphatic and Aromatic Alkynes with Iodoaryls." Synlett Jun. 2008, 2008, 886-888, 3 pages.

Tambade et al., "Phosphane-Free Palladium-Catalyzed Carbonylative Suzuki Coupling Reaction of Aryl and Heteroaryl Iodides." European Journal of Organic Chemistry 2009.18, 2009, 3022-3025, 4 pages.

Tao et al., "Palladium complexes bearing an N-heterocyclic carbene-sulfonamide ligand for cooligomerization of ethylene and polar monomers." Journal of Polymer Science Part A: Polymer Chemistry 57.3, 2019, 474-477, 4 pages.

Taylor et al., "Metal-free Synthesis of Ynones from Acyl Chlorides and Potassium Alkynyltrifluoroborate Salts." JoVE (Journal of Visualized Experiments) 96, e52401, 2015, 9 pages.

Touj et al., "Correction: Efficient in situ N-heterocyclic carbene palladium (ii) generated from Pd (OAc) 2 catalysts for carbonylative Suzuki coupling reactions of arylboronic acids with 2-bromopyridine under inert conditions leading to unsymmetrical arylpyridine ketones: synthesis, characterization and cytotoxic activities." RSC Advances 9.2, 2019, 16 pages.

Wang et al., "Carbonylative Suzuki cross-coupling reaction catalyzed by bimetallic Pd-Pt nanodendrites under ambient CO pressure." Catalysis Communications 101, 2017, 10-14, 21 pages.

Wang et al., "Cross-linked polymer supported palladium catalyzed carbonylative Sonogashira coupling reaction in water," Tetrahedron letters 52.14, 2011, 1587-1591, 5 pages.

Wang et al., "N-heterocyclic carbene-palladium (II) complexes with benzoxazole or benzothiazole ligands: Synthesis, characterization, and application to Suzuki-Miyaura cross-coupling reaction." Journal of Organometallic Chemistry 804, 2016, 73-79, 24 page.

Wu et al., "A General Palladium-Catalyzed Carbonylative Sonogashira Coupling of Aryl Triflates." Chemistry—A European Journal 17.1, 2011, 106-110, 5 pages.

Wu et al., "Palladium-catalyzed carbonylative coupling of benzyl chlorides with terminal alkynes to give 1, 4-diaryl-3-butyn-2-ones and related furanones." Organic & Biomolecular Chemistry 9.23, 2011, 8003-8005, 3 pages.

Zhang et al., "Aryl-palladium-NHC complex: efficient phosphine-free catalyst precursors for the carbonylation of aryl iodides with amines or alkynes." Organic & Biomolecular Chemistry 12.47, 2014, 9702-9706, 5 pages.

Zhang et al., "Chiral linker-bridged bis-N-heterocyclic carbenes: design, synthesis, palladium complexes, and catalytic properties." Dalton Transactions 45.29, 2016, 11699-11709, 14 pages.

Zheng et al., "Highly efficient N-Heterocyclic carbene-palladium complex-catalyzed multicomponent carbonylative Suzuki reaction: novel practical synthesis of unsymmetric aryl ketones." Applied Organometallic Chemistry 21.9, 2007, 772-776, 5 pages.

Zhiping et al., "Synthesis of propylene carbonate from alcoholysis of urea catalyzed by modified hydroxyapatites." Chinese Journal of Catalysis 31.4, 2010, 3 pages.

Astakhov et al., "A new mode of operation of Pd-NHC systems studied in a catalytic Mizoroki-Heck reaction," Organometallics 36.10, May 2017, 1981-1992, 12 pages.

Chernyshev et al., "Revealing the unusual role of bases in activation/deactivation of catalytic systems: O-NHC coupling in M/NHC catalysis." Chemical science 9.25, May 2018, 5564-5577, 14 pages.

Gupta et al., "Benzimidazole-based palladium-N-heterocyclic carbene: a useful catalyst for C-C cross-coupling reaction at ambient condition," Tetrahedron 69.1, Jan. 2013, 122-128, 7 pages.

(56) References Cited

OTHER PUBLICATIONS

Han et al., "Syntheses and characterizations of Pd (II) complexes incorporating a N-heterocyclic carbene and aromatic N-heterocycles." Organometallics 26.25, Dec. 2007, 6447-6452, 6 pages.

Huynh et al., "Palladium (II) Complexes of a Sterically Bulky, Benzannulated N-Heterocyclic Carbene with Unusual Intramolecular C-H⊙⊙⊙ Pd and Ccarbene⊙⊙⊙ Br Interactions and Their Catalytic Activities." Organometallics 25.13, Jun. 2006, 3267-3274, 8 pages.

Kaloğlu et al., "The first used butylene linked bis (N-heterocyclic carbene)-palladium-PEPPSI complexes in the direct arylation of furan and pyrrole." Journal of Organometallic Chemistry 915, Jun. 2020, 10 pages.

Liu et al., "NHC PdII Complex Bearing 1, 6-Hexylene Linker: Synthesis and Catalytic Activity in the Suzuki-Miyaura and Heck-Mizoroki Reactions." European Journal of Organic Chemistry Jul. 2013, Mar. 2013, 1253-1261, 9 pages.

Yadav et al., "Well-Defined N-Heterocyclic Carbene-Palladium Complexes as Efficient Catalysts for Domino Sonogashira Coupling/Cyclization Reaction and C-H bond Arylation of Benzothiazole." Applied Organometallic Chemistry 33.7, Jul. 2019, 11 pages.

PCT International Search Report and Written Opinion in International Appln. No. PCT/US2021/055153, dated Jan. 26, 2022, 16 pages.

PCT International Search Report and Written Opinion in International Appln. No. PCT/US2021/058733, dated Feb. 9, 2022, 15 pages.

SYNTHESIS OF ALKYNONES VIA CARBONYLATIVE SONOGASHIRA COUPLING REACTIONS CATALYZED BY PD(II)-N-HETEROCYCLIC CARBENE-PYRIDINE COMPLEXES

TECHNICAL FIELD

This document relates to N-substituted Pd(II)-N-heterocyclic carbene-pyridine complexes. The document also relates to use of the complexes in carbonylative Sonogashira coupling reactions to form alkynones.

BACKGROUND

Alkynyl ketones, or alkynones, have utility as synthetic intermediates, particularly for the synthesis of heterocyclic systems that can be used as precursors in the synthesis of anti-cancer and anti-fungal products. Alkynones have also found use in the polymer industry. A common route for the synthesis of these compounds is the carbonylative Sonogashira coupling reaction. The reaction is typically catalyzed by a palladium complex and a large excess of an amine base. High catalyst loading, for example, greater than 1 mol % of the palladium complex is often required. This can lead to higher costs and less efficient reactions.

Therefore, there is a need for a palladium complex that can catalyze a Sonogashira coupling reaction, in particular, a carbonylative Sonogashira coupling reaction, that has high catalytic activity, is stable, and requires low catalyst loading.

SUMMARY

Provided in the present disclosure is a compound of Formula (I):

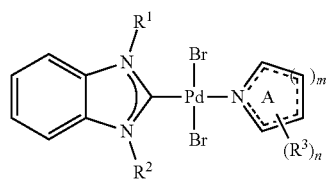

wherein:
R$^1$ is selected from C$_1$-C$_{10}$ alkyl, C$_5$-C$_{10}$ cycloalkyl, aryl, and (C$_1$-C$_3$ alkylene)-aryl;
R$^2$ is selected from C$_1$-C$_{10}$ alkyl, C$_5$-C$_{10}$ cycloalkyl, aryl, and (C$_1$-C$_3$ alkylene)-aryl;
R$^3$ is selected from C$_1$-C$_{10}$ alkyl, C$_5$-C$_{10}$ cycloalkyl, aryl, and (C$_1$-C$_3$ alkylene)-aryl;
n is 0, 1, 2, 3, 4, or 5;
m is 1 or 2; and
===== represents a single or double bond.

In some embodiments of the compound of Formula (I), R$^1$ is C$_1$-C$_6$ alkyl. In some embodiments, R$^1$ is selected from methyl, ethyl, propyl, isopropyl, and butyl. In some embodiments, R$^1$ is isopropyl.

In some embodiments of the compound of Formula (I), R$^2$ is selected from C$_1$-C$_6$ alkyl, C$_3$-C$_{10}$ cycloalkyl, and (C$_1$-C$_3$ alkylene)-aryl. In some embodiments, R$^2$ is selected from isopropyl, benzyl, and adamantyl.

In some embodiments of the compound of Formula (I), n is 0.

In some embodiments of the compound of Formula (I), m is 2. In some embodiments, ring A is

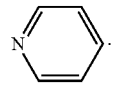

In some embodiments, the compound of Formula (I) is selected from:

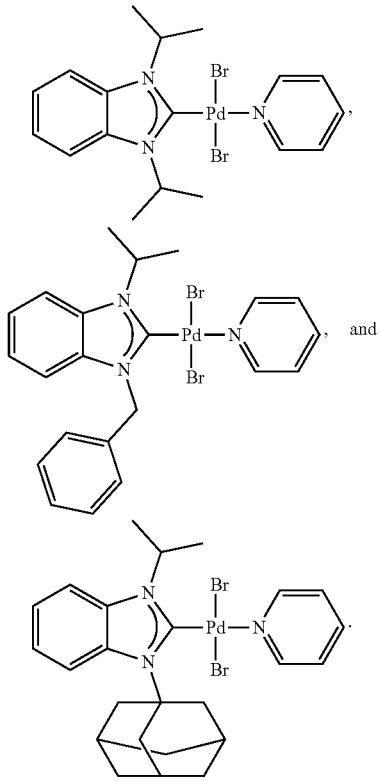

Also provided in the present disclosure is a compound of Formula (II)

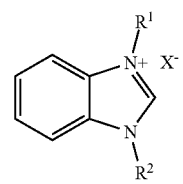

wherein:
R$^1$ is selected from C$_1$-C$_{10}$ alkyl, C$_5$-C$_{10}$ cycloalkyl, aryl, and (C$_1$-C$_3$ alkylene)-aryl;
R$^2$ is selected from C$_1$-C$_{10}$ alkyl, C$_5$-C$_{10}$ cycloalkyl, aryl, and (C$_1$-C$_3$ alkylene)-aryl; and
X is a halide.

In some embodiments of the compound of Formula (II), R$^1$ is C$_1$-C$_6$ alkyl. In some embodiments, R$^1$ is selected from methyl, ethyl, propyl, isopropyl, and butyl. In some embodiments, R$^1$ is isopropyl.

In some embodiments of the compound of Formula (II), $R^2$ is selected from $C_1$-$C_6$ alkyl, $C_3$-$C_{10}$ cycloalkyl, and ($C_1$-$C_3$ alkylene)-aryl. In some embodiments, $R^2$ is selected from isopropyl, benzyl, and adamantyl.

In some embodiments, the compound of Formula (II) is selected from:

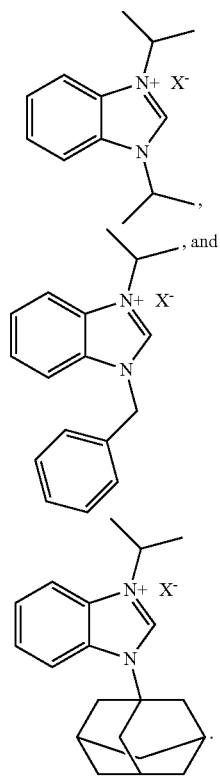

Also provided in the present disclosure is a method of preparing a compound of Formula (I):

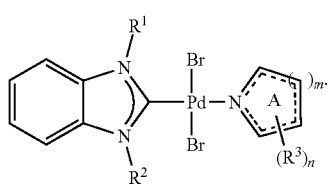

the method comprising reacting a compound of Formula (II)

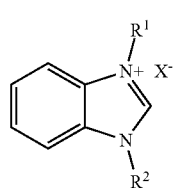

with pyridine in the presence of a palladium catalyst, wherein:

$R^1$ is selected from $C_1$-$C_{10}$ alkyl, $C_5$-$C_{10}$ cycloalkyl, aryl, and ($C_1$-$C_3$ alkylene)-aryl;

$R^2$ is selected from $C_1$-$C_{10}$ alkyl, $C_5$-$C_{10}$ cycloalkyl, aryl, and ($C_1$-$C_3$ alkylene)-aryl.

In some embodiments of the method, $R^1$ is isopropyl.

In some embodiments of the method, $R^2$ is selected from isopropyl, benzyl, and adamantyl.

In some embodiments of the method, the compound of Formula (I) is selected from:

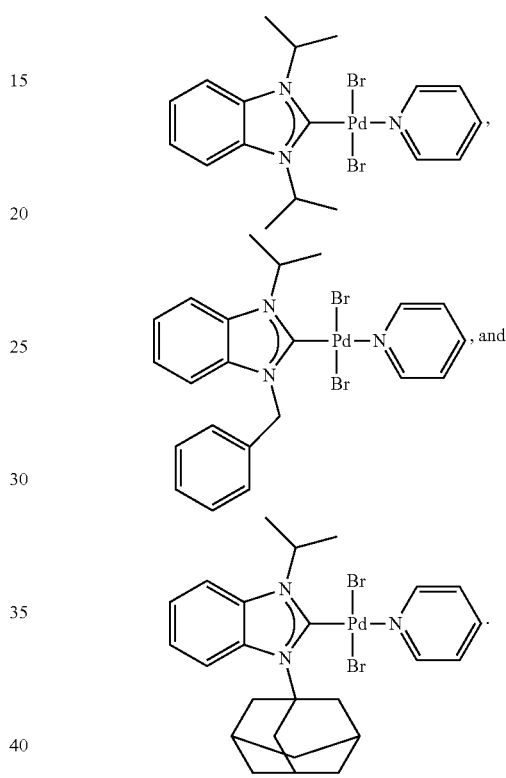

In some embodiments of the method, the palladium catalyst is palladium bromide.

Also provided in the present disclosure is a method of preparing an alkynone, the method comprising contacting an aryl halide and an alkyne with a compound of Formula (I) in the presence of a CO source.

In some embodiments of the method, the aryl halide is a compound having the formula:

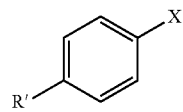

wherein:

X is selected from F, Cl, Br, and I; and

R' is selected from —H, —O—($C_1$-$C_3$ alkyl), —NO$_2$, and —C(=O)—($C_1$-$C_3$ alkyl).

In some embodiments of the method, wherein X is I.

In some embodiments of the method, the alkyne is a compound having the formula:

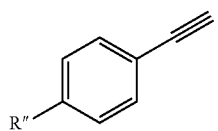

wherein R″ is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl.

In some embodiments of the method, the alkyne is a compound having the formula:

wherein R‴ is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl.

In some embodiments of the method, the alkynone is a compound having the formula:

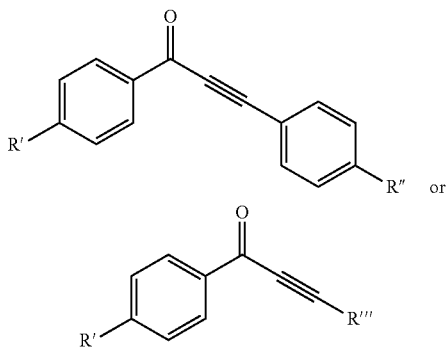

or a pharmaceutically acceptable salt thereof.

In some embodiments of the method, the compound of Formula (I) is selected from:

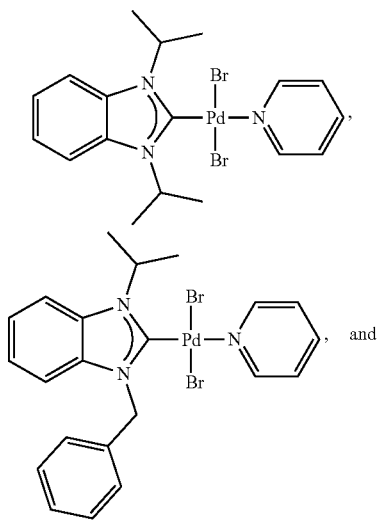

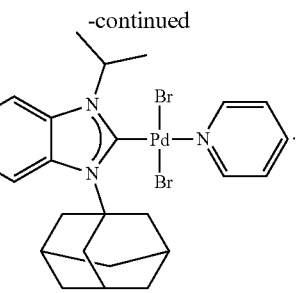

In some embodiments of the method, the compound of Formula (I) is present in an amount of about 0.01 mol % to about 1.0 mol %.

DETAILED DESCRIPTION

The present disclosure relates to N-heterocyclic carbene (NHC)-pyridine ligands and palladium-NHC-pyridine complexes. The palladium-NHC-pyridine complexes exhibit high catalytic activity and efficiency with low catalyst loading. For example, the palladium-NHC-pyridine complexes exhibit high catalytic efficiency in the synthesis of alkynones via carbonylative Sonogashira coupling reactions. In some embodiments, the coupling reaction is between an aryl halide or aryl dihalide with an aryl alkyne, alkyl alkyne, or dialkyne. The resulting alkynones can be useful precursors in the synthesis of anti-cancer and anti-fungal products. The alkynones can also be used in the polymer industry.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Definitions

In this disclosure, the terms "a," "an," and "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about" as used herein can allow for a degree of variability in a value or range, for example, within 10%, within 5%, or within 1% of a stated value or of a stated limit of a range.

In the methods described in the present disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "cycloalkyl" means a non-aromatic cyclic ring system containing only carbon atoms in the ring system backbone, such as cyclopropyl, cyclobutyl, cyclopentyl, cyclohexyl, and cyclohexenyl. Cycloalkyl may include multiple fused rings. Cycloalkyl may have any degree of saturation provided that none of the rings in the ring system are aromatic. Cycloalkyl groups can either be unsubstituted or substituted with one or more substituents. In some embodiments, cycloalkyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, and 2,3-dihydro-1H-indenyl. In some embodiments, the aryl is phenyl.

As used herein, the term "heteroaryl" means a mono- or bicyclic group having 5 to 10 ring atoms, such as 5, 6, 8, 9, or 10 ring atoms, such as 5, 6, 9, or 10 ring atoms; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrrolo[2,3-6]pyridinyl, quinazolinyl, quinolinyl, thieno[2,3-c]pyridinyl, pyrazolo[3,4-6]pyridinyl, pyrazolo[3,4-c]pyridinyl, pyrazolo[4,3-c]pyridine, pyrazolo[4,3-6]pyridinyl, tetrazolyl, chromane, 2,3-dihydrobenzofuran, tetrahydroquinoline, and isoindoline. In some embodiments, the heteroaryl is selected from thienyl, pyridinyl, furyl, pyrazolyl, imidazolyl, isoindolinyl, pyranyl, pyrazinyl, and pyrimidinyl.

As used herein, "heterocyclyl" means a 3-14 membered, such as 3-11 membered, such as 3-8 membered nonaromatic mono-, bi- or tricyclic group comprising at least one heteroatom in the ring system backbone. Bicyclic and tricyclic heterocyclyl groups may include fused ring systems, spirocyclic ring systems, and bridged ring systems and may include multiple fused rings. In some embodiments, heterocyclyls have one to four heteroatom(s) independently selected from N, O, and S. In some embodiments, heterocyclyls have one to three heteroatom(s) independently selected from N, O, and S. In some embodiments, heterocyclyls have one to two heteroatom(s) independently selected from N, O, and S. In some embodiments, monocyclic heterocyclyls are 3-membered rings. In some embodiments, monocyclic heterocyclyls are 4-membered rings. In some embodiments, monocyclic heterocyclyls are 5-membered rings. In some embodiments, monocyclic heterocyclyls are 6-membered rings. In some embodiments, monocyclic heterocyclyls are 7-membered rings. As used herein, "monocyclic heterocyclyl" means a single nonaromatic cyclic ring comprising at least one heteroatom in the ring system backbone. Examples of heterocyclyls include aziridinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, and thiomorpholinyl. In some embodiments, the heterocyclyl is selected from azetidinyl, morpholinyl, piperazinyl, pyrrolidinyl, and tetrahydropyridinyl. As used herein, "bicyclic heterocyclyl" means a nonaromatic bicyclic ring system comprising at least one heteroatom in the ring system backbone. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, 2-oxa-5-azabicyclo[2.2.1]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, and 2-azabicyclo[2.2.2]octane. As used herein, "spirocyclic heterocyclyl" means a nonaromatic bicyclic ring system comprising at least one heteroatom in the ring system backbone and with the rings connected through just one atom. Examples of spirocyclic heterocyclyls include 2-azaspiro[2.2]pentane, 2-oxa-6-azaspiro[3.3]heptane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[3.5]nonane, 2,7-diazaspiro[3.5]nonane, 1,7-diazaspiro[4.5]decane, 2,5-diazaspiro[3.6]decane, 1-oxa-8-azaspiro[4.5]decane, 2-oxa-8-azaspiro[4.5]decane.

Compounds of Formula (I)

Provided in the present disclosure is a compound of Formula (I)

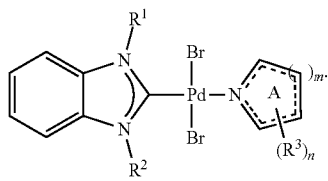
(I)

wherein:

$R^1$ is selected from $C_1$-$C_{10}$ alkyl, $C_5$-$C_{10}$ cycloalkyl, aryl, and ($C_1$-$C_3$ alkylene)-aryl;

$R^2$ is selected from $C_1$-$C_{10}$ alkyl, $C_5$-$C_{10}$ cycloalkyl, aryl, and ($C_1$-$C_3$ alkylene)-aryl;

$R^3$ is selected from $C_1$-$C_{10}$ alkyl, $C_5$-$C_{10}$ cycloalkyl, aryl, and ($C_1$-$C_3$ alkylene)-aryl;

n is 0, 1, 2, 3, 4, or 5;

m is 1 or 2; and

===== represents a single or double bond.

In some embodiments of the compound of Formula (I), $R^1$ is $C_1$-$C_{10}$ alkyl. In some embodiments, $R^1$ is $C_1$-$C_6$ alkyl. In some embodiments, $R^1$ is selected from methyl, ethyl, propyl, isopropyl, and butyl. In some embodiments, $R^1$ is isopropyl. In some embodiments, the $C_1$-$C_6$ alkyl group is optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^1$ is $C_5$-$C_{10}$ cycloalkyl. In some embodiments, $R^1$ is selected from cyclopentyl and cyclohexyl. In some embodiments, the $C_5$-$C_{10}$ cycloalkyl group is optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^1$ is aryl.

In some embodiments of the compound of Formula (I), $R^1$ is ($C_1$-$C_3$ alkylene)-aryl. In some embodiment, $R^1$ is benzyl.

In some embodiments of the compound of Formula (I), $R^2$ is selected from $C_1$-$C_{10}$ alkyl, $C_5$-$C_{10}$ cycloalkyl, aryl, and ($C_1$-$C_3$ alkylene)-aryl. In some embodiments, $R^2$ is selected from isopropyl, benzyl, and adamantyl. In some embodiments, $R^2$ is isopropyl. In some embodiments, $R^2$ is benzyl. In some embodiments, $R^2$ is adamantyl.

In some embodiments of the compound of Formula (I), $R^2$ is $C_1$-$C_{10}$ alkyl. In some embodiments, $R^2$ is $C_1$-$C_6$ alkyl. In some embodiments, $R^2$ is selected from methyl, ethyl, propyl, isopropyl, butyl, sec-butyl, iso-butyl, tert-butyl, pentyl, and hexyl. In some embodiments, $R^2$ is isopropyl. In some embodiments, the $C_1$-$C_{10}$ alkyl group is optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^2$ is $C_5$-$C_{10}$ cycloalkyl. In some embodiments, $R^2$ is selected from cyclopentyl, cyclohexyl, and adamantyl. In some embodiments, $R^2$ is adamantyl. In some embodiments, the $C_5$-$C_{10}$ cycloalkyl group is optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^2$ is ($C_1$-$C_3$ alkylene)-aryl. In some embodiments, $R^2$ is selected from benzyl, —($CH_2$)$_2$-aryl, and —($CH_2$)$_3$-aryl. In some embodiments, $R^2$ is benzyl. In some embodiments, the $C_1$-$C_3$ alkylene group and the aryl group are each optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (I), $R^1$ is $C_1$-$C_6$ alkyl and $R^2$ is selected from $C_1$-$C_6$ alkyl, $C_5$-$C_{10}$ cycloalkyl, and ($C_1$-$C_3$ alkylene)-aryl. In some embodiments, $R^1$ is $C_1$-$C_6$ alkyl and $R^2$ is $C_1$-$C_6$ alkyl. In some embodiments, $R^1$ is isopropyl and $R^2$ is isopropyl. In some embodiments, $R^1$ is $C_1$-$C_6$ alkyl and $R^2$ is $C_5$-$C_{10}$ cycloalkyl. In some embodiments, $R^1$ is isopropyl and $R^2$ is adamantyl. In some embodiments, $R^1$ is $C_1$-$C_6$ alkyl and $R^2$ is ($C_1$-$C_3$ alkylene)-aryl. In some embodiments, $R^1$ is isopropyl and $R^2$ is benzyl.

In some embodiments of the compound of Formula (I), n is 0. In some embodiments, n is 1. In some embodiments, n is 2. In some embodiments, n is 3. In some embodiments, n is 4. In some embodiments, n is 5.

In some embodiments, m is 1. In some embodiments, m is 1 and ring A is:

In some embodiments, m is 1, n is 0, and ring A is:

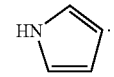

In some embodiments, m is 2. In some embodiments, m is 2 and ring A is:

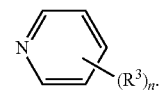

In some embodiments, m is 2, n is 0, and ring A is:

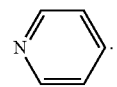

In some embodiments, the compound of Formula (I) is selected from:

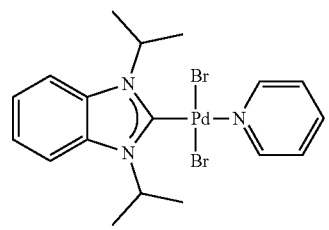

,

-continued

In some embodiments, the compound of Formula (I) is

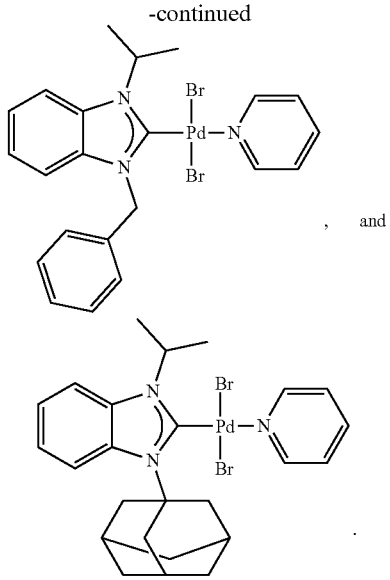

In some embodiments, the compound of Formula (I) is

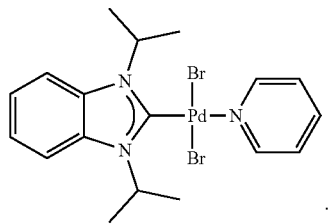

In some embodiments, the compound of Formula (I) is

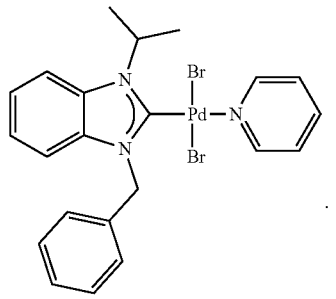

In some embodiments, the compound of Formula (I) is

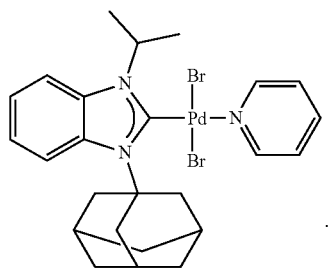

Compounds of Formula (II)

Also provided in the present disclosure are compounds of Formula (II)

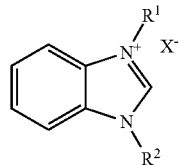

wherein:

$R^1$ is selected from $C_1$-$C_{10}$ alkyl, $C_5$-$C_{10}$ cycloalkyl, aryl, and ($C_1$-$C_3$ alkylene)-aryl;

$R^2$ is selected from $C_1$-$C_{10}$ alkyl, $C_5$-$C_{10}$ cycloalkyl, aryl, and ($C_1$-$C_3$ alkylene)-aryl; and X is a halide.

In some embodiments of the compound of Formula (II), $R^1$ is $C_1$-$C_{10}$ alkyl. In some embodiments, $R^1$ is $C_1$-$C_6$ alkyl. In some embodiments, $R^1$ is selected from methyl, ethyl, propyl, isopropyl, and butyl. In some embodiments, $R^1$ is isopropyl. In some embodiments, the $C_1$-$C_6$ alkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^1$ is $C_5$-$C_{10}$ cycloalkyl. In some embodiments, $R^1$ is selected from cyclopentyl and cyclohexyl. In some embodiments, the $C_5$-$C_{10}$ cycloalkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^1$ is aryl.

In some embodiments of the compound of Formula (II), $R^1$ is ($C_1$-$C_3$ alkylene)-aryl. In some embodiment, $R^1$ is benzyl.

In some embodiments of the compound of Formula (II), $R^2$ is selected from $C_1$-$C_{10}$ alkyl, $C_5$-$C_{10}$ cycloalkyl, aryl, and ($C_1$-$C_3$ alkylene)-aryl. In some embodiments, $R^2$ is selected from isopropyl, benzyl, and adamantyl. In some embodiments, $R^2$ is isopropyl. In some embodiments, $R^2$ is benzyl. In some embodiments, $R^2$ is adamantyl.

In some embodiments of the compound of Formula (II), $R^2$ is $C_1$-$C_{10}$ alkyl. In some embodiments, $R^2$ is $C_1$-$C_6$ alkyl. In some embodiments, $R^2$ is selected from methyl, ethyl, propyl, isopropyl, butyl, sec-butyl, iso-butyl, tert-butyl, pentyl, and hexyl. In some embodiments, $R^2$ is isopropyl. In some embodiments, the $C_1$-$C_{10}$ alkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^2$ is $C_5$-$C_{10}$ cycloalkyl. In some embodiments, $R^2$ is selected from cyclopentyl cyclohexyl, and adamantyl. In some embodiments, $R^2$ is adamantyl. In some embodiments, the $C_5$-$C_{10}$ cycloalkyl group is optionally substituted with one or more substituents independently selected from halogen, —CN, —OH, —NH$_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^2$ is ($C_1$-$C_3$ alkylene)-aryl. In some embodiments, $R^2$ is selected from benzyl, —($CH_2$)$_2$-aryl, and —($CH_2$)$_3$-aryl. In some embodiments, $R^2$ is benzyl. In some embodiments, the $C_1$-$C_3$ alkylene group and the aryl group are each optionally substituted with one or more substituents independently selected from halogen, —CN, —OH, —$NH_2$, $C_1$-$C_3$ alkyl, $C_1$-$C_3$ haloalkyl, $C_3$-$C_6$ cycloalkyl, —O—($C_1$-$C_3$ alkyl), ($C_1$-$C_3$ alkylene)-O—($C_1$-$C_3$ alkyl), and aryl.

In some embodiments of the compound of Formula (II), $R^1$ is $C_1$-$C_6$ alkyl and $R^2$ is selected from $C_1$-$C_6$ alkyl, $C_5$-$C_{10}$ cycloalkyl, and ($C_1$-$C_3$ alkylene)-aryl. In some embodiments, $R^1$ is $C_1$-$C_6$ alkyl and $R^2$ is $C_1$-$C_6$ alkyl. In some embodiments, $R^1$ is isopropyl and $R^2$ is isopropyl. In some embodiments, $R^1$ is $C_1$-$C_6$ alkyl and $R^2$ is $C_5$-$C_{10}$ cycloalkyl. In some embodiments, $R^1$ is isopropyl and $R^2$ is adamantyl. In some embodiments, $R^1$ is $C_1$-$C_6$ alkyl and $R^2$ is ($C_1$-$C_3$ alkylene)-aryl. In some embodiments, $R^1$ is isopropyl and $R^2$ is benzyl.

In some embodiments of the compound of Formula (II), X is a halide. In some embodiments, X is selected from F, Cl, Br, and I. In some embodiments, X is Br.

In some embodiments, the compound of Formula (II) is selected from:

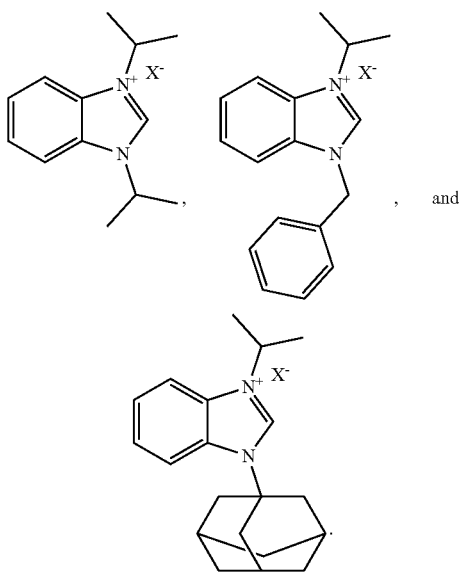

In some embodiments, the compound of Formula (II) is:

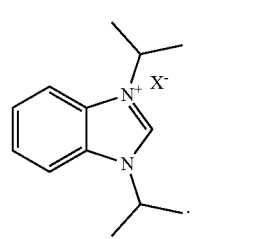

In some embodiments, the compound of Formula (II) is:

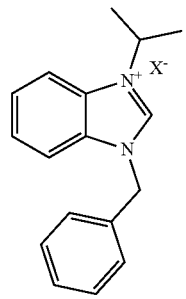

In some embodiments, the compound of Formula (II) is:

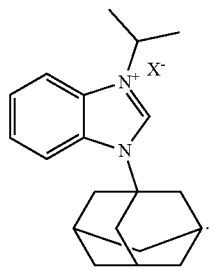

Method of Preparing Compounds of Formula (I) and Formula (II)

Also provided in the present disclosure are methods of preparing compounds of Formula (I) and Formula (II). In some embodiments, the method includes reacting a compound of Formula (II), such as a compound of Formula (II) as described in the present disclosure, with pyridine in the presence of a palladium catalyst, to form a compound of Formula (I). In some embodiments, the compound of Formula (I) is isolated. In some embodiments, the compound of Formula (I) is purified.

In some embodiments, the palladium catalyst is selected from the group consisting of palladium bromide, palladium chloride, palladium iodide, and palladium sulfate. In some embodiments, the palladium catalyst is palladium bromide.

In some embodiments, the compounds of Formula (I) are prepared according to the general scheme presented in Scheme 1, where $R^1$, $R^2$, and X are as described elsewhere in this disclosure.

Scheme 1

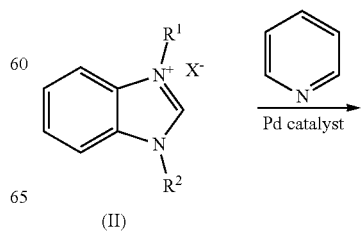

(II)

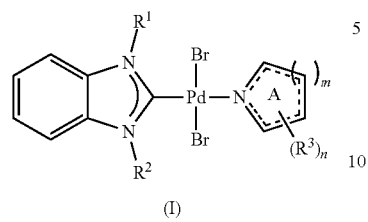

(I)

In some embodiments, the method includes preparing a compound of Formula (II). In some embodiments, the method includes reacting a substituted 1H-benzo[d]imidazole with a substituted halide to form a compound of Formula (II). In some embodiments, the compound of Formula (II) is isolated. In some embodiments, the compound of Formula (II) is purified. In some embodiments, the compound of Formula (II) is isolated and purified prior to using in the method of preparing compounds of Formula (I).

In some embodiments, the substituted halide has the formula $R^1$—X, where $R^1$ and X are as described elsewhere in this disclosure.

In some embodiments, the compound of Formula (II) is prepared according to the general scheme presented in Scheme 2, where $R^1$, $R^2$, $R^3$, X, m, and n are as described elsewhere in this disclosure.

Scheme 2

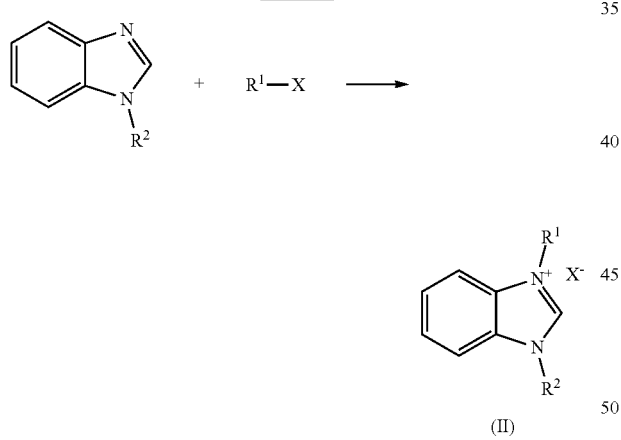

(II)

In some embodiments, the methods of the present disclosure are used to prepare a compound of Formula (I), where the compound of Formula (I) is selected from

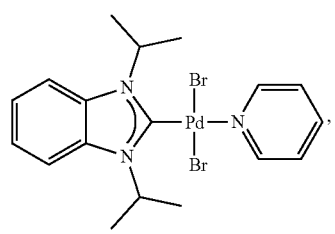

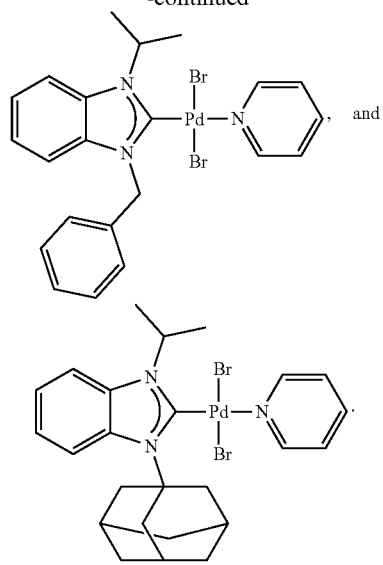

In some embodiments, the methods of present disclosure are used to prepare a compound of Formula (II), where the compound of Formula (II) is selected from

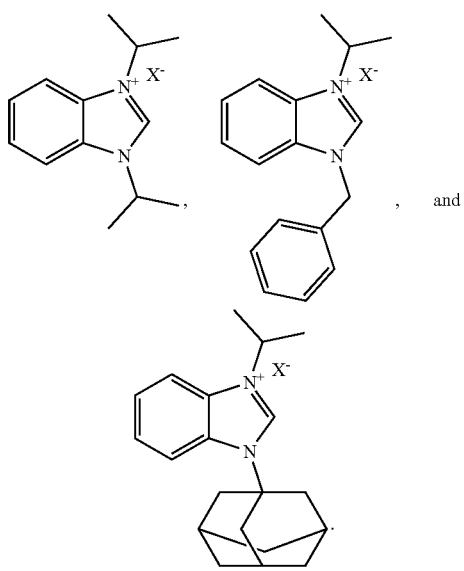

Methods of Preparing Alkynones

The compounds of Formula (I) of the present disclosure are useful as catalysts. For example, the compounds of Formula (I) can be used as catalysts for the synthesis of alkynones, including aryl alkynones and alkyl alkynones. In some embodiments, the compounds of Formula (I) are used as a catalyst in a carbonylative Sonogashira coupling reaction. In some embodiments, the carbonylative Sonogashira coupling reaction is between an aryl halide or aryl dihalide and an aryl alkyne, alkyl alkyne, or dialkyne. In some embodiments, the carbonylative Sonogashira coupling reaction is between an aryl bromide, aryl iodide, or aryl diiodide and an aryl alkyne, alkyl alkyne, or dialkyne.

In some embodiments, the alkynones of the present disclosure are prepared according to the general scheme presented in Scheme 3, where R—X can be an aryl halide, aryl dihalide, or vinyl halide, and R'—C≡C can be an aryl alkyne, alkyl alkyne, or dialkyne.

Scheme 3

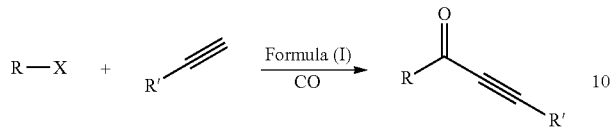

Thus, provided in the present disclosure is a method of preparing an alkynone, the method including contacting an aryl halide, aryl dihalide, or vinyl halide and an alkyne with a compound of Formula (I) as described in the present disclosure in the presence of a CO source.

In some embodiments, the method includes contacting an aryl halide and an alkyne with a compound of Formula (I) as described in the present disclosure in the presence of a CO source. In some embodiments, the aryl halide is a compound having the formula:

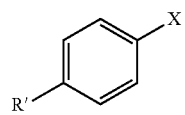

wherein:

X is selected from F, Cl, Br, and I; and

R' is selected from —H, —O—($C_1$-$C_3$ alkyl), —$NO_2$, and —C(=O)—($C_1$-$C_3$ alkyl).

In some embodiments, X is Br. In some embodiments, X is I.

In some embodiments, R' is —H. In some embodiments, R' is —$OCH_3$. In some embodiments, R' is —$NO_2$. In some embodiments, R' is —C(=O)$CH_3$.

In some embodiments, the method includes contacting an aryl halide and an alkyne with a compound of Formula (I) as described in the present disclosure in the presence of a CO source. In some embodiments, the alkyne is a compound having the formula:

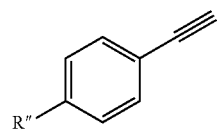

wherein R" is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl. In some embodiments, R" is —H. In some embodiments, R" is $C_1$-$C_6$ alkyl. In some embodiments, R" is methyl. In some embodiments, R" is ethyl. In some embodiments, R" is propyl. In some embodiments, R" is butyl. In some embodiments, R" is tert-butyl. In some embodiments, R" is pentyl. In some embodiments, R" is hexyl. In some embodiments, R" is decyl. In some embodiments, R" is —$OCH_3$. In some embodiments, R" is $C_3$-$C_6$ cycloalkyl. In some embodiments, R" is cyclopropyl. In some embodiments, R" is cyclobutyl. In some embodiments, R" is cyclopentyl. In some embodiments, R" is cyclohexyl. In some embodiments, R" is aryl. In some embodiments, R" is —$CH_2$-cyclohexyl. In some embodiments, R" is ($C_1$-$C_3$ alkyl)-aryl. In some embodiments, R" is benzyl. In some embodiments, R" is —$(CH_2)_2$-aryl. In some embodiments, R" is —$(CH_2)_3$-aryl.

In some embodiments, the alkyne is a compound having the formula:

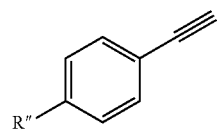

wherein R'" is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl. In some embodiments, R" is —H. In some embodiments, R" is $C_1$-$C_6$ alkyl. In some embodiments, R" is methyl. In some embodiments, R" is ethyl. In some embodiments, R" is propyl. In some embodiments, R" is butyl. In some embodiments, R" is tert-butyl. In some embodiments, R" is pentyl. In some embodiments, R" is hexyl. In some embodiments, R" is decyl. In some embodiments, R" is —$OCH_3$. In some embodiments, R" is $C_3$-$C_6$ cycloalkyl. In some embodiments, R" is cyclopropyl. In some embodiments, R" is cyclobutyl. In some embodiments, R" is cyclopentyl. In some embodiments, R" is cyclohexyl. In some embodiments, R" is aryl. In some embodiments, R" is —$CH_2$-cyclohexyl. In some embodiments, R" is ($C_1$-$C_3$ alkyl)-aryl. In some embodiments, R" is benzyl. In some embodiments, R" is —$(CH_2)_2$-aryl. In some embodiments, R" is —$(CH_2)_3$-aryl.

In some embodiments of the method of producing an alkynone, the compound of Formula (I) is a compound of Formula (I) of the present disclosure. In some embodiments, the compound of Formula (I) is selected from:

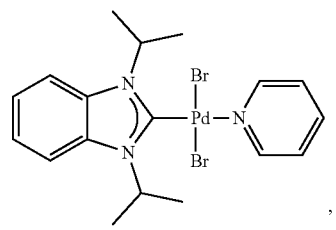

,

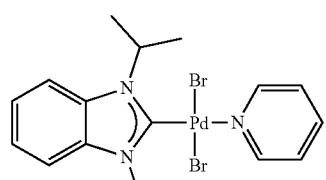

, and

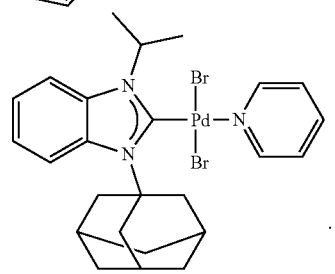

.

The compounds of Formula (I) have high catalytic efficiency and activity and allow for low catalyst loading. In some embodiments, less than or about 1 mol % of the compound of Formula (I) is required to catalyze a reaction, such as a carbonylative Sonogashira coupling reaction. In some embodiments, the amount of catalyst (compound of Formula (I)) used in the carbonylative Sonogashira coupling reaction is about 0.01 mol % to about 1 mol %, such as about 0.01 mol % to about 0.99 mol %, about 0.01 mol % to about 0.9 mol %, about 0.01 mol % to about 0.8 mol %, about 0.01 mol % to about 0.7 mol %, about 0.01 mol % to about 0.6 mol %, about 0.01 mol % to about 0.5 mol %, about 0.01 mol % to about 0.4 mol %, about 0.01 mol % to about 0.3 mol %, about 0.01 mol % to about 0.2 mol %, about 0.01 mol % to about 0.1 mol %, about 0.01 mol % to about 0.05 mol %, about 0.01 mol % to about 0.03 mol %, about 0.03 mol % to about 1 mol %, 0.03 mol % to about 0.99 mol %, about 0.03 mol % to about 0.9 mol %, about 0.03 mol % to about 0.8 mol %, about 0.03 mol % to about 0.7 mol %, about 0.03 mol % to about 0.6 mol %, about 0.03 mol % to about 0.5 mol %, about 0.03 mol % to about 0.4 mol %, about 0.03 mol % to about 0.3 mol %, about 0.03 mol % to about 0.2 mol %, about 0.03 mol % to about 0.1 mol %, about 0.03 mol % to about 0.05 mol %, about 0.05 mol % to about 1 mol %, 0.05 mol % to about 0.99 mol %, about 0.05 mol % to about 0.9 mol %, about 0.05 mol % to about 0.8 mol %, about 0.05 mol % to about 0.7 mol %, about 0.05 mol % to about 0.6 mol %, about 0.05 mol % to about 0.5 mol %, about 0.05 mol % to about 0.4 mol %, about 0.05 mol % to about 0.3 mol %, about 0.05 mol % to about 0.2 mol %, about 0.05 mol % to about 0.1 mol %, about 0.1 mol % to about 1 mol %, 0.1 mol % to about 0.99 mol %, about 0.1 mol % to about 0.9 mol %, about 0.1 mol % to about 0.8 mol %, about 0.1 mol % to about 0.7 mol %, about 0.1 mol % to about 0.6 mol %, about 0.1 mol % to about 0.5 mol %, about 0.1 mol % to about 0.4 mol %, about 0.1 mol % to about 0.3 mol %, about 0.1 mol % to about 0.2 mol %, about 0.2 mol % to about 1 mol %, 0.2 mol % to about 0.99 mol %, about 0.2 mol % to about 0.9 mol %, about 0.2 mol % to about 0.8 mol %, about 0.2 mol % to about 0.7 mol %, about 0.2 mol % to about 0.6 mol %, about 0.2 mol % to about 0.5 mol %, about 0.2 mol % to about 0.4 mol %, about 0.2 mol % to about 0.3 mol %, about 0.3 mol % to about 1 mol %, 0.3 mol % to about 0.99 mol %, about 0.3 mol % to about 0.9 mol %, about 0.3 mol % to about 0.8 mol %, about 0.3 mol % to about 0.7 mol %, about 0.3 mol % to about 0.6 mol %, about 0.3 mol % to about 0.5 mol %, about 0.3 mol % to about 0.4 mol %, about 0.4 mol % to about 1 mol %, 0.4 mol % to about 0.99 mol %, about 0.4 mol % to about 0.9 mol %, about 0.4 mol % to about 0.8 mol %, about 0.4 mol % to about 0.7 mol %, about 0.4 mol % to about 0.6 mol %, about 0.4 mol % to about 0.5 mol %, about 0.5 mol % to about 1 mol %, 0.5 mol % to about 0.99 mol %, about 0.5 mol % to about 0.9 mol %, about 0.5 mol % to about 0.8 mol %, about 0.5 mol % to about 0.7 mol %, about 0.5 mol % to about 0.6 mol %, about 0.6 mol % to about 1 mol %, 0.6 mol % to about 0.99 mol %, about 0.6 mol % to about 0.9 mol %, about 0.6 mol % to about 0.8 mol %, about 0.6 mol % to about 0.7 mol %, about 0.7 mol % to about 1 mol %, 0.7 mol % to about 0.99 mol %, about 0.7 mol % to about 0.9 mol %, about 0.7 mol % to about 0.8 mol %, about 0.8 mol % to about 1 mol %, 0.8 mol % to about 0.99 mol %, about 0.8 mol % to about 0.9 mol %, about 0.9 mol % to about 1 mol %, 0.9 mol % to about 0.99 mol %, or about 0.01 mol %, about 0.03 mol %, about 0.05 mol %, about 0.1 mol %, about 0.15 mol %, about 0.2 mol %, about 0.25 mol %, about 0.3 mol %, about 0.35 mol %, about 0.4 mol %, about 0.45 mol %, about 0.5 mol %, about 0.55 mol %, about 0.6 mol %, about 0.65 mol %, about 0.7 mol %, about 0.75 mol %, about 0.8 mol %, about 0.85 mol %, about 0.9 mol %, about 0.95 mol %, about 0.99 mol %, or about 1 mol %. In some embodiments, the compound of Formula (I) is present in an amount of about 0.01 mol % to about 1.0 mol %. In some embodiments, the compound of Formula (I) is present in an amount of about 0.01 mol % to about 0.5 mol %. In some embodiments, the compound of Formula (I) is present in an amount of about 0.01 mol % to about 0.05 mol %. In some embodiments, the compound of Formula (I) is present in an amount of about 0.1 mol % to about 0.25 mol %. In some embodiments, the compound of Formula (I) is present in an amount of about 0.03 mol %. In some embodiments, the compound of Formula (I) is present in an amount of about 0.2 mol %. Without wishing to be bound by any particular theory, it is believed that the increased catalytic activity of the compound of Formula (I) allows for the use of smaller amounts of the catalyst as compared to other palladium-based catalysts that have lower catalytic activity. For example, the amount of the compound of Formula (I) can be less than or about 1 mol %, which is less than the amount of about 1 mol % to about 5 mol % required by other palladium-based catalysts with lower catalytic activity.

In some embodiments of the methods of producing alkynones as described in the present disclosure, any suitable CO source can be used. In some embodiments, the CO source is carbon monoxide gas.

The alkynones of the present disclosure have utility as precursors in the synthesis of products such as anti-cancer agents and anti-fungal agents. The alkynones of the present disclosure can also be used in the polymer industry. In some embodiments, the method produces an alkynone having the formula:

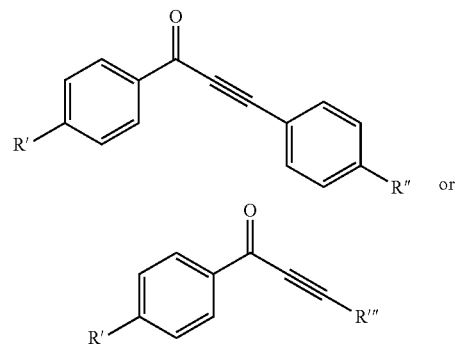

or a pharmaceutically acceptable salt thereof.

In some embodiments, the alkynone is a compound having the formula

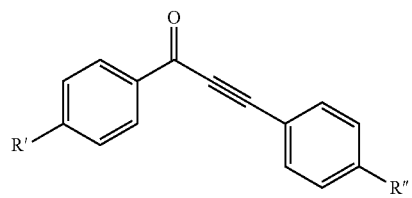

or a pharmaceutically acceptable salt thereof.

In some embodiments, the alkynone is a compound having the formula

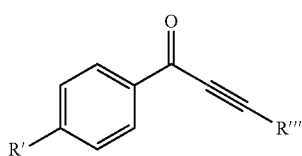

or a pharmaceutically acceptable salt thereof.

EXAMPLES

Example 1—Synthesis of palladium(II)-N-heterocyclic carbene-pyridine (Pd—NHC-Py) Complexes A series of palladium(II)-N-heterocyclic carbene-pyridine (Pd-NHC-Py) complexes (Pd-C1, Pd-C2 and Pd-C3) were prepared in several steps from 1H-benzo[d]imidazole.

Synthesis of alkyl-1H-benzo[d]imidazoles

Alkyl-1H-benzo[d]imidazoles BZ1 and BZ2 were prepared according to Scheme 4.

Scheme 4

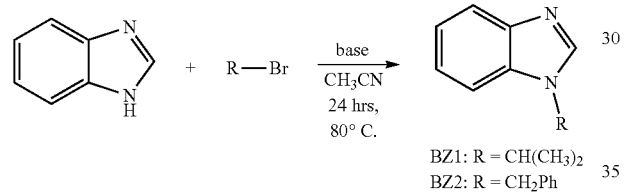

BZ1: R = CH(CH3)2
BZ2: R = CH2Ph

Briefly, the 1-alkyl benzimidazoles (BZ1 and BZ2) were prepared by the following procedure: Benzimidazole (10.0 mmol) was introduced into a clean and dry round bottom flask with an excess amount of alkyl bromide (12.2 mmol) (2-bromopropane or benzyl bromide). Potassium hydroxide (20.0 mmol) or cesium carbonate (20.0 mmol) with 1 mmol of TBAB (tetrabutylammonium bromide) was used as a base for 2-bromopropane and benzyl bromide, respectively. The mixture was dissolved in 100 mL of distilled acetonitrile and stirred for 24 hrs at 80° C. The reaction was monitored by TLC (1/1: ethyl acetate/hexanes) until no unreacted benzimidazole was observed. The solvent was then removed by a rotary evaporator. The oily product was purified by extraction twice with 30 mL of ethyl acetate and 20 mL of distilled water. The aqueous layer was separated and washed with ethyl acetate and the combined organic layers were dried and washed several times with n-hexane.

1-Isopropyl-1H-benzo[d]imidazole (BZ1)

Yield=77%. Sticky brown oil product. $^1$H NMR (400 MHz, CDCl$_3$) δ (ppm): 7.85 (s, 1H, N$_2$CH$_{bim}$), 7.64-7.62 (m, 1H, Ar—H), 7.25-7.22 (m, 1H, Ar—H), 7.11-7.08 (m, 2H, Ar—H), 4.42 (sep, 1H, $^3$J=6.76 Hz, NCH) 1.40 (d, 6H, $^3$J=6.76 Hz, NC(CH$_3$)$_2$); $^{13}$C{$^1$H} NMR (125 MHz, CDCl$_3$) δ (ppm): 143.5 (NCN), 139.8, 132.7, 122.1, 121.5, 119.8, 109.7, (Ar—H), 47.2 (NCH), 22.02 [NC(CH$_3$)$_2$]. Anal. Calcd for C$_{10}$H$_{12}$N$_2$ (160): C, 74.97%; H, 7.55%; N, 17.48%. Found: C, 74.84%; H, 7.23%; N, 17.93%.

1-Benzyl-1H-benzo[d]imidazole (BZ2)

Yield 87%; light yellow solid; $^1$H NMR (500 MHz, CDCl$_3$) δ (ppm): 7.98 (s, 1H, N$_2$CH$_{bim}$), 7.83 (d, 1H, $^3$J=7.63 Hz, Ar—H), 7.34-7.24 (m, 6H, Ar—H), 7.18 (d, 2H, $^3$J=7.02 Hz, Ar—H), 5.36 (m, 2H, NCH$_2$-Ph); $^{13}$C{$^1$H} NMR (125 MHz, CDCl$_3$) δ (ppm); 143.1 (NCN), 135.4, 129, 128.3, 127.06, 123.1, 122.3, 120.3, 110.04 (Ar—H), 48.8 (NCH$_2$). Anal. Calcd for C$_{14}$H$_{12}$N$_2$ (208.26): C, 80.74%; H, 5.81%; N, 13.45%. Found: C, 80.79%; H, 5.63%; N, 13.58%.

Alkyl-1H-benzo[d]imidazoles BZ3 was prepared according to Scheme 5.

Scheme 5

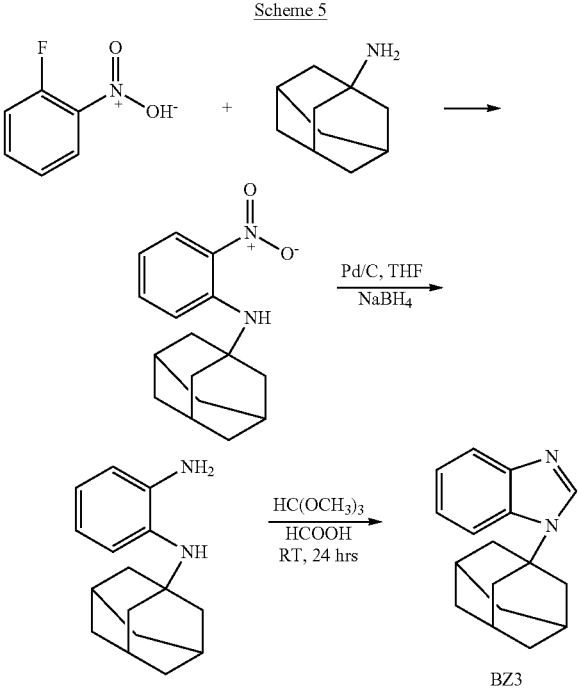

BZ3

1-Adamantyl benzimidazole (BZ3) was synthesized as follows. 2-Fluoronitrobenzene (10.0 mmol) was added to 1-adamantylamine (14.5 mmol) and anhydrous potassium fluoride (13.3 mmol) under argon in a 50 mL schlenk purged and flamed under vacuum. After 3 vacuum/argon cycles, the mixture was heated, stirred at 180° C. for 48 hrs, and cooled to room temperature. Dichloromethane was added to the reaction mixture followed by the addition of water. The organic phase was washed with brine and water, followed by drying on sodium sulfate and concentrated under vacuum. The crude mixture was purified on silica gel using a dichloromethane/hexane mixture (2/10) affording a yellow-orange solid (0.178 g, 92%) of ortho-nitro-1-adamantylaniline. The reduction of ortho-nitro-1-adamantylaniline was achieved using sodium borohydride to produce ortho-aminoadamantyl aniline. The reduction process started by dissolving 10.0 mmol of ortho-nitro-1-adamantylaniline in THF and then 0.250 mmol of Pd/C was added carefully. The resulting slurry was stirred and NaBH4 (25.0 mmol) was added portion-wise. The obtained solid was then filtered and extracted three times using a mixture of ethyl acetate and H2O. To fully dry the solid, anhydrous sodium sulfate was added and the solid filtered off and evaporated to dryness to yield ortho-aminoadamantyl aniline (76%) as a dark oil.

Finally, a round-bottom flask was charged with ortho-aminoadamantyl aniline (8.80 mmol), anhydrous tetrahydrofuran (THF), trimethyl orthoformate (6.60 mmol) and formic acid (0.880 mmol). The mixture was stirred overnight at room temperature. Solvents were evaporated and the crude product was purified by chromatography to yield the N-adamantyl-1H-benzo[d]imidazole (BZ3) (85%).

1-(adamantan-1-yl)-1H-benzo[d]imidazole (BZ3)

Yield 85%; light brown solid; NMR (500 MHz, DMSO-$d^6$) δ (ppm): 8.22 (s, 1H, $N_2CH_{bimi}$), 7.85 (m, 1H, Ar—H), 7.64 (m, 1H, Ar—H), 7.18 (m, 2H, Ar—H), 2.33 (m, 6H, $3CH_2$), 2.21 (m, 3H, 3CH), 1.81-1.75 (m, 6H, NC $3CH_2$); $^{13}C\{^1H\}$ NMR (125 MHz, DMSO-d6) δ (ppm); 140.8 (NCN), 121.6, 121.1, 119.8, 113.9 (Ar—H), 56.6 (NC), 41.13 $NC(C)_3$, 35.45 $C(CH)CH_2$, 28.98 $CH(CH_2)CH$. Anal. Calcd for $C_{17}H_{20}N_2$ (252.36): C, 80.91%; H, 7.99%; N, 11.10%. Found: C, 80.73%; H, 7.76%; N, 11.51%.

Synthesis of NHC Ligand Precursors

NHC ligand precursors NHC-1, NHC-2, and NHC-3 were prepared from BZ1, BZ2, and BZ3, respectively, as shown in Scheme 6.

Scheme 6

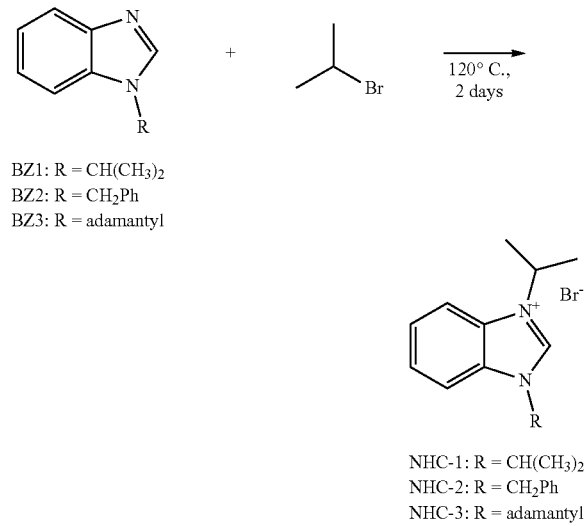

BZ1: R = $CH(CH_3)_2$
BZ2: R = $CH_2Ph$
BZ3: R = adamantyl

NHC-1: R = $CH(CH_3)_2$
NHC-2: R = $CH_2Ph$
NHC-3: R = adamantyl

NHC-1, NHC-2, and NHC-3 were prepared by charging the appropriate 1-alkyl benzimidazole (BZ1, BZ2, or BZ3) (1.00 mmol) and 2-bromopropane (3.00 mL) into a pressure tube. The mixture was stirred for 48 hours at 120° C. and then cooled down to room temperature. For NHC-1 and NHC-3 cases, the filtration was used to collect the products as solid precipitates and then washed several times with diethyl ether (5 mL). The pure product was dried under vacuum. For NHC-2, a brown sticky mixture was obtained. Based on the ionic nature of the product, a careful extraction under a fume hood with 5 mL of water (three times) was carried out. The aqueous layer was collected, and water was evaporated under vacuum. The product was obtained as orange crystals.

1,3-Diisopropylbenzimidazole-3-ium Bromide (NHC-1)

Yield=65%. White solid. $^1$H NMR (400 MHz, $CDCl_3$) δ (ppm): 11.35 (s, 1H, $N_2CH_{bimi}$), 7.80-7.78 (m, 2H, C—H arom), 7.65-7.63 (m, 2H, C—H arom), 5.19 (sep, 2H, $^3J=6.8$ Hz, NCH), 1.85 (d, 12H, $^3J=6.8$ Hz, $2(CH_3)_2$); $^{13}$C NMR (125 MHz, $CDCl_3$) δ (ppm): 140.69, 130.85, 126.89, 113.90 (C arom); 52.39 $2C(CH_3)_2$, 22.24, $2(CH_3)_2$, GC-MS m/z 283.2 ($M^r$). Anal. Calc. for $C_{13}H_1BrN_2$, (283.21): C, 55.13%; H, 6.76%; N, 9.89%. Found: C, 55.41; H, 7.02; N, 10.03. ESI-MS: m/z 202.17 [M−Br]$^+$.

1-Benzyl-3-isopropyl-1H-benzo[d]imidazol-3-ium Bromide (NHC-2)

Yield=85%.

Orange crystalline solid. $^1$H NMR (400 MHz, $CDCl_3$) δ (ppm): 11.51 (s, 1H, $N_2C$—$H_{bimi}$), 7.78 (d, 1H, $^3J=8.00$ Hz, C—H arom), 7.65-7.51 (m, 5H, C—H arom), 7.35-7.29 (m, 3H, C—H-(aryl)), 5.97 (s, 2H, $CH_2$-Ph), 5.03 (sep, 1H, $^3J=6.4$ Hz, NCH), 1.83 (d, 6H, $^3J=6.4$ Hz, $NC(CH_3)_2$); $^{13}$C NMR (125 MHz, $CDCl_3$) δ (ppm): 141.31, 132.99, 131.51, 130.77, 129.27, 129.10, 128.52, 127.26, 127.14, 114.08, 113.64 (C arom), 51.95 ($NCH_2$), 51.37 ($NCH_2$), 22.44 ($2(CH_3)_2$). Anal. Calc. for $C_{17}H_{19}BrN_2$, (331.26): C, 61.64%; H, 5.78%; N, 8.46%. Found: C, 62.051; H, 5.93; N, 8.80. MS: m/z 331.2 ($M^r$). ESI-MS; m/z 251.2 [M−Br]$^+$.

1-(Adamantan-1-yl)-3-isopropyl-1H-benzo[d]imidazol-3-ium Bromide (NHC-3)

Yield=88%. Light brown solid. $^1$H NMR (400 MHz, $CDCl_3$) δ (ppm): 10.82 (s, 1H, $N_2C$—$H_{bimi}$), 8.03 (d, 1H, $^3J=8$ Hz, C—H arom), 7.2 (d, 1H, J=7.0 Hz, C—H arom), 7.63-7.57 (m, 2H, C—H arom), 5.61 (sep, 1H, $^3J=6.4$ Hz, CH), 2.55 (m, 6H, $3CH_{2adam}$), 2.41 (m, 3H, $3CH_{Adam}$), 1.87-1.85 (m, 12H, $\{3CH_{2Adam}\}+\{2CH_3\}$); $^{13}$C NMR (125 MHz, $CDCl_3$) δ (ppm): 140.22, 131.44, 130.49, 126.31, 126.04, 116.77, 114.59 (C arom), 63.02 $NC(C)_3$, 52.86 $C(CH_3)_2$ 41.72 $C(CH_2)_3$, 35.58 3(CH), 29.54 [$3(CH_2)$, $C(CH_3)_2$]. Anal. Calc. for $C_{20}H_{27}BrN_2$, (375.35): C, 64.00%; H, 7.25%; N, 7.46%. Found: C, 64.321; H, 7.53; N, 7.80. MS: m/z 375 ($M^r$); ESI-MS; m/z 294.2 [M−Br]$^+$.

Synthesis of palladium(II)-NHC-pyridine Complexes

Pd-NHC-Py complexes Pd-1, Pd-2, and Pd-3 were prepared from NHC-1, NHC-2, and NHC-3, respectively, as shown in Scheme 7.

Scheme 7

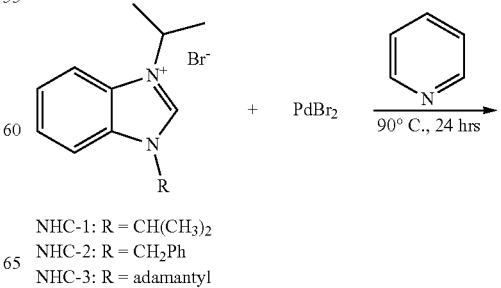

NHC-1: R = $CH(CH_3)_2$
NHC-2: R = $CH_2Ph$
NHC-3: R = adamantyl

-continued

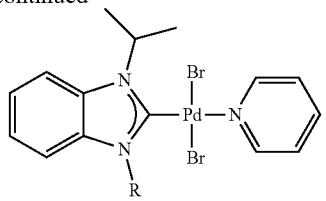

Pd-C1: R = CH(CH₃)₂
Pd-C2: R = CH₂Ph
Pd-C3: R = adamantyl

Pd-C1, Pd-C2, and Pd-C3 were prepared by reacting palladium bromide with 1.0 equivalent of the appropriate ligand precursor (NHC-1, NHC-2 and NHC-3) and an excess amount of pyridine. Briefly, a round bottom flask (15 mL) was charged with the appropriate N-heterocyclic carbene ligand precursor (NHC-1, NHC-2, or NHC-3) (0.50 mmol), palladium (II) bromide (0.50 mmol), potassium carbonate (2.0 mmol) and pyridine (5 mL). The reaction mixture was heated to 90° C. for 24 hrs under stirring. After cooling down to room temperature, the colloidal crude product was diluted with 5 mL of dichloromethane and the mixture was purified by passing through a short silica column covered with a short pad of Celite. The flash column was eluted with distilled methanol. The solvents were evaporated using rotary evaporator. The complexes were washed with ether, collected and dried at room temperature under vacuum. The complexes were obtained as yellow crystals. A slow crystallization procedure was followed in the preparation of single crystals for these complexes. A saturated solution of the palladium was prepared in dichloromethane/acetonitrile (8/1) (v/v). The disappearance of the acidic C-2 protons of the benzimidazole rings, which were initially present in the N-substituted imidazolium salts, was used to confirm the formation of the Pd-NHC complexes. The appearance of new signals at 156-158 ppm in the $^{13}$C NMR spectra of the three complexes assignable to the palladated carbon Pd-C was a further indication of the palladation of the NHC ligand precursors.

(1,3-Diisopropyl-1,3-dihydro-2H-benzo[d]imidazol-2-ylidene)(pyridin-1(2H)-yl)palladium(II) Bromide (Pd-C1)

Yield=77%. Yellow solid. $^1$H NMR (400 MHz, CDCl₃) δ (ppm): 9.07-9.06 (m, 2H, C—H-pyr), 7.73-7.70 (m, 1H, C—H-pyr), 7.53-7.52 (m, 2H, C—H arom), 7.31-7.29 (m, 2H, C—H arom), 7.16-7.15 (m, 2H, C—H pyr), 6.27 (sep, 2H, $^3$J=7.2 Hz, NCH), 1.73 (d, 12H, $^3$J=7.2 Hz, 4CH₃), $^{13}$C NMR (125 MHz, CDCl₃) δ (ppm): 158.14 (Pd-C), 151.56, 136.71, 132.31, 123.34, 121.04, 111.43 (C arom); 53.38 [C(CH₃)₂], 19.41 (2CH₃). Calc. for C₁₈H₂₃Br₂N₃Pd, (547.63): C, 39.48%; H, 4.23%; N, 7.67%. Found: C, 40.05; H, 4.62; N, 7.94. ESI-MS: m/z 467.12 [M−Br]⁺.

(1-Benzyl-3-isopropyl-1,3-dihydro-2H-benzo[d]imidazol-2-ylidene)(pyridin-1(2H)-yl)palladium(II) Bromide (Pd-C2)

Yield=74%. Yellow crystals. $^1$H NMR (400 MHz, CDCl₃) δ (ppm): $^1$H NMR (400 MHz, CDCl₃) δ (ppm): δ (ppm): 9.06-9.05 (m, 2H, C—H pyr), 7.71-7.69 (m, 1H, C—H pyr), 7.48 (m, 2H, C—H arom), 7.45-7.41 (m, 5H, C—H arom), 7.35-7.29 (m, 2H, C—H aryl), 7.13-7.09 (m, 3H, C—H pyr), 5.87 (s, 1H, CH₂-Ph), 5.30 (m, 1H, NCH), 1.67 (m, 6H, NC(CH₃)₂); $^{13}$C NMR (125 MHz, CDCl₃) δ (ppm): 154.34 (Pd-C), 153.4, 138.51, 128.82, 128.12, 127.26, 127.14, 125.04, 122.78, 112.33, 110.69 (C arom), 53.47 (NCH₂), 51.37 (NCH₂), 21.44 [(CH₃)₂]. Anal. Calc. for C₂₂H₂₃Br₂N₃Pd, (595.68): C, 44.36%; H, 3.39%; N, 7.05%. Found: C, 43.85; H, 4.13; N, 7.48; ESI-MS: m/z 515.11 [M−Br]⁺.

(1-(Adamantan-1-yl)-3-isopropyl-1,3-dihydro-2H-benzo[d]imidazol-2-ylidene)(pyridin-1(2H)-yl)palladium(II) Bromide (Pd-C3)

Yield=86%. Light yellow crystals. $^1$H NMR (400 MHz, CDCl₃) δ (ppm): 9.11-9.10 (m, 2H, C—H pyr), 8.87 (d, 1H, $^3$J=7.8 Hz, C—H arom), 7.81-7.77 (m, 1H, C—H pyr), 7.64 (d, 1H, $^3$J=7.4 Hz, C—H arom), 7.39-7.36 (m, 2H, C—H arom), 7.25-7.18 (m, 2H, C—H-pyr), 7.11 (sep, 1H, $^3$J=7 Hz, NCH), 3.24 (m, 6H, 3CH₂_Adam), 2.43 (m, 3H, 3CH_Adam), 1.98 (m, 3H, 3CH_Adam), 1.85-1.83 (m, 9H, {3CH_Adam+2CH₃}); $^{13}$C NMR (125 MHz, CDCl₃) δ (ppm): 156.78 (Pd-C), 152.95, 137.78, 135.03, 133.17, 124.64, 122.04, 121.33, 115.71, 112.72 (C arom), 61.78 NC(C)₃, 57.16 C(CH₃)₂ 42.61 C(CH₂)₃, 36.17 3(CH), 30.26 3(CH₂), 20.24 C(CH₃)₂. Anal. Calc. for C₂₅H₃₁Br₂N₃Pd, (639.77): C, 46.93%; H, 4.88%; N, 6.57%. Found: C, 47.32; H, 5.33; N, 7.13. ESI-MS: m/z 559.09 [M−Br]⁺.

Example 2—Carbonylative Sonogashira Coupling Reactions

The palladium(II)-N-heterocyclic carbene-pyridine (Pd-NHC-Py) complexes Pd-C1, Pd-C2 and Pd-C3 prepared according to Example 1 were used in carbonylative Sonogashira coupling reactions to produce alkynones. The Pd-NHC-Py catalysts displayed high catalytic activity with low catalyst loading. The reactions required only 0.03 mol % of the Pd-NHC-Py complex and produced alkynones in high yield.

Synthesis of Aryl Alkynones Using Pd-C1, Pd-C2, and Pd-C3

An aryl alkynone was synthesized by reacting 4-iodoanisole (1.0 mmol) with arylacetylene (1.5 mmol) in the presence of 0.03 mol % catalyst Pd-C1, Pd-C2, or Pd-C3, Et3N (2.0 mmol), and CO (200 psi) in toluene (3 mL) at 100° C. for 3 hours, as shown in Scheme 8 and Table 1.

Scheme 8

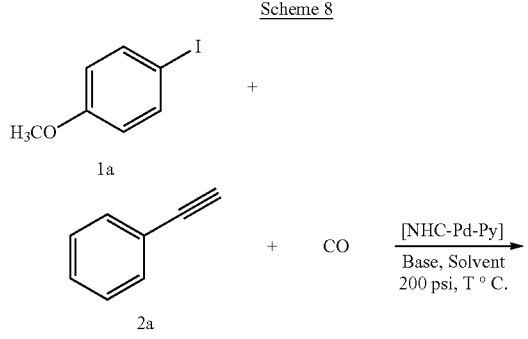

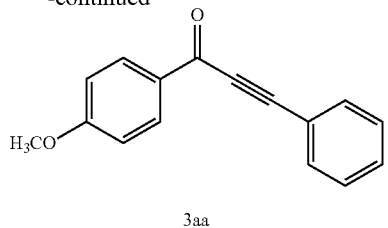

3aa

TABLE 1

| Entry | NHC—Pd—Py (mol %) | Isolated Yield 3aa (%) |
|---|---|---|
| 1 | Pd—C1 (0.03) | 85 |
| 2 | Pd—C2 (0.03) | 79 |
| 3 | Pd—C3 (0.03) | 97 |

Synthesis of Aryl Alkynones Using Pd-C3

A series of aryl alkynones was synthesized by reacting aryl iodides with functionalized aryl alkynes in the presence of the Pd-C3 catalyst as shown in Scheme 9 and Table 2.

Scheme 9

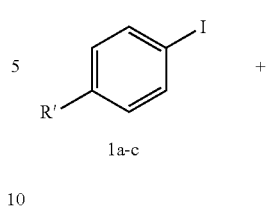

TABLE 2

| Entry | Aryl Iodide 1 | Aryl Alkyne 2 | Carbonylative Sonogashira 3 | Isolated Yield (%) |
|---|---|---|---|---|
| 1 | 1a | 2a | 3a | 97 |
| 2 | 1a | 2b | 3b | 94 |
| 3 | 1a | 2c | 3c | 96 |
| 4 | 1b | 2a | 3d | 98 |

TABLE 2-continued

| Entry | Aryl Iodide 1 | Aryl Alkyne 2 | Carbonylative Sonogashira 3 | Isolated Yield (%) |
|---|---|---|---|---|
| 5 | 1c | 2a | 3e | 95 |

The carbonylative coupling reaction was performed by reacting aryl iodides 1a-1c with functionalized aryl alkynes 2a-2c in the presence of 0.03 mol % of Pd-C3, with 2.0 equivalents of Et3N, 3 mL of toluene, 200 psi CO, at 100° C. for 3 hrs. Alkynones 3a-3e were produced in excellent yields (94-98%) via the carbonylative Sonogashira coupling reaction.

Synthesis of Alkyl Alkynones Using Pd-C3

A series of alkyl alkynones was synthesized by reacting aryl iodides with alkyl alkynes in the presence of the Pd-C3 catalyst as shown in Scheme 10.

Scheme 10

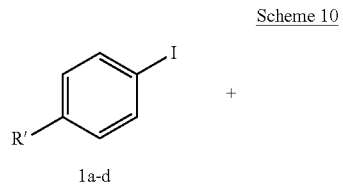

1a-d

+

4a-h $\xrightarrow{\text{CO, [Pd-C3]}}_{\text{Et}_3\text{N, toluene, 200 psi, 100° C.}}$ 5a-h The carbonylative coupling reaction was performed by reacting aryl iodides 1a-1d with alkyl alkynes 4a-4h in the presence of 0.20 mol % of Pd-C3, with 2.0 equivalents of Et3N, 3 mL of toluene, 200 psi CO, at 100° C. for 18 hrs. Alkynones 5a-5i were produced in high yields (67-95%) via the carbonylative Sonogashira coupling reaction as shown in Table 3.

TABLE 3

| Aryl Iodide 1a-d | Alkyl Alkyne 4a-h | Product 5ba-da | Isolated Yield (%) |
|---|---|---|---|
| 1b | 4a | 5a | 89 |
| 1b | 4b | 5b | 92 |
| 1b | 4c | 5c | 95 |

TABLE 3-continued
| Aryl Iodide 1a-d | Alkyl Alkyne 4a-h | Product 5ba-da | Isolated Yield (%) |
|---|---|---|---|
| 1a | 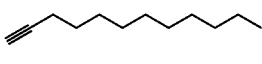 4d | 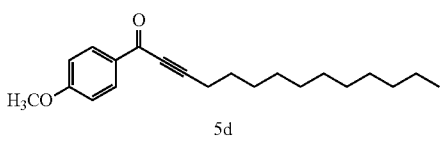 [SMILES: CCCCCCCCCCCC#CC(=O)c1ccc(OC)cc1] 5d | 87 |
| 1a | 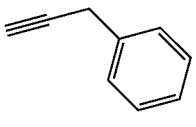 4f | 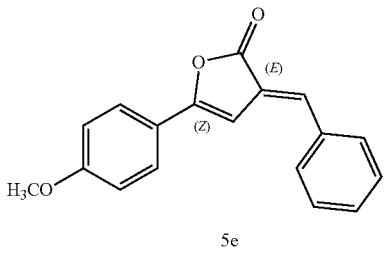 [SMILES: COc1ccc(C2=C/C(=C\c3ccccc3)C(=O)O2)cc1] 5e | 94 |
| 1a | 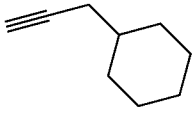 4g | 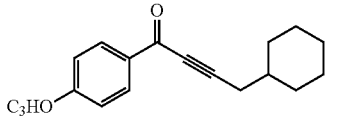 5f | 67 |
| 1c[a] | 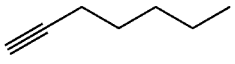 4a | 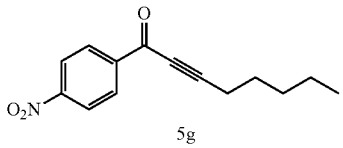 [SMILES: CCCCCC#CC(=O)c1ccc([N+](=O)[O-])cc1] 5g | 93 |
| 1c[a] | 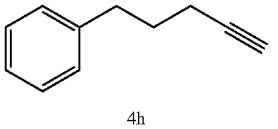 4h | 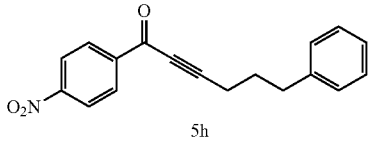 [SMILES: O=C(C#CCCCc1ccccc1)c1ccc([N+](=O)[O-])cc1] 5h | 76 |
| 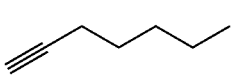 1d[a] | 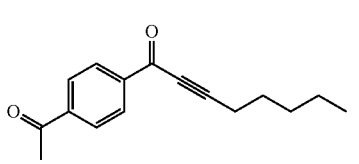 4a | (structure) 5i | 96 |
[a]Time = 6 hrs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I)

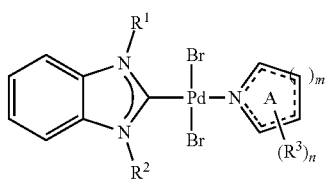

wherein:
  $R^1$, $R^2$, and $R^3$ are each independently selected from $C_1$-$C_{10}$ alkyl, $C_5$-$C_{10}$ cycloalkyl, aryl, and ($C_1$-$C_3$ alkylene)-aryl, with the proviso that $R^1$ and $R^2$ are different when ring A is pyridine;
  n is 0, 1, 2, 3, 4, or 5;
  m is 1 or 2; and
  ≈≈≈ represents a single or double bond.

2. The compound of claim 1, wherein $R^1$ is $C_1$-$C_6$ alkyl.

3. The compound of claim 2, wherein $R^1$ is selected from methyl, ethyl, propyl, isopropyl, and butyl.

4. The compound of claim 3, wherein $R^1$ is isopropyl.

5. The compound of claim 1, wherein $R^2$ is selected from $C_1$-$C_6$ alkyl, $C_3$-$C_{10}$ cycloalkyl, and ($C_1$-$C_3$ alkylene)-aryl.

6. The compound of claim 5, wherein $R^2$ is selected from isopropyl, benzyl, and adamantyl.

7. The compound of claim 1, wherein n is 0.

8. The compound of claim 1, wherein m is 2.

9. The compound of claim 8, wherein ring A is

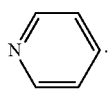

10. The compound of claim 1, wherein the compound of Formula (I) is selected from:

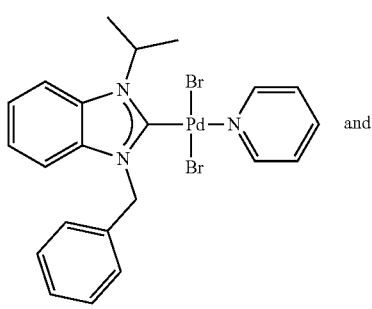

and

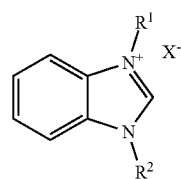

11. A compound of Formula (II)

(II)

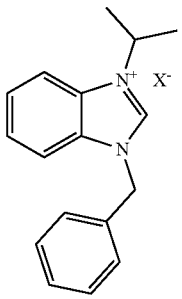

wherein:
  $R^1$ and $R^2$ are each independently selected from $C_1$-$C_{10}$alkyl, $C_5$-$C_{10}$ cycloalkyl, aryl, and ($C_1$-$C_3$ alkylene)-aryl, with the proviso that $R^1$ and $R^2$ are different;
  and
  X is a halide.

12. The compound of claim 11, wherein $R^1$ is $C_1$-$C_6$ alkyl.

13. The compound of claim 12, wherein $R^1$ is selected from methyl, ethyl, propyl, isopropyl, and butyl.

14. The compound of claim 13, wherein $R^1$ is isopropyl.

15. The compound of claim 11, wherein $R^2$ is selected from $C_1$-$C_6$ alkyl, $C_3$-$C_{10}$ cycloalkyl, and ($C_1$-$C_3$ alkylene)-aryl.

16. The compound of claim 15, wherein $R^2$ is selected from isopropyl, benzyl, and adamantyl.

17. The compound of claim 11, wherein the compound of Formula (II) is selected from:

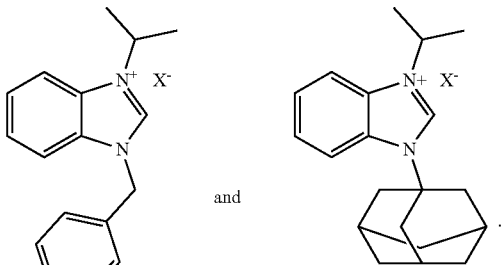

18. A method of preparing a compound of Formula (I)

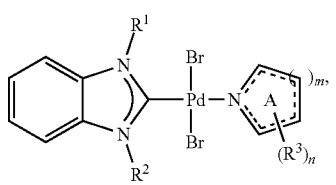

the method comprising reacting a compound of Formula (II)

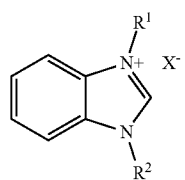

with pyridine in the presence of a palladium catalyst, wherein:

$R^1$ and $R^2$ are each independently selected from $C_1$-$C_{10}$ alkyl, $C_5$-$C_{10}$ cycloalkyl, aryl, and ($C_1$-$C_3$ alkylene)-aryl, with the proviso that $R^1$ and $R^2$ are different.

19. The method of claim 18, wherein $R^1$ is isopropyl.

20. The method of claim 18, wherein $R^2$ is selected from isopropyl, benzyl, and adamantyl.

21. The method of claim 18, wherein the compound of Formula (I) is selected from:

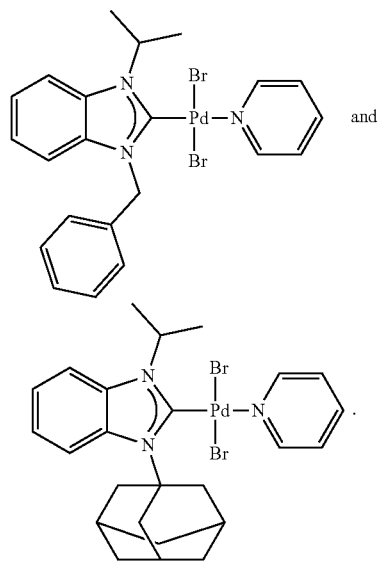

22. The method of claim 18, wherein the palladium catalyst is palladium bromide.

23. A method of preparing an alkynone, comprising contacting an aryl halide and an alkyne with a compound of Formula (I) according to claim 1 in the presence of a CO source.

24. The method of claim 23, wherein the aryl halide is a compound having the formula:

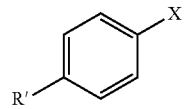

wherein:

X is selected from F, Cl, Br, and I; and

R' is selected from —H, —O—($C_1$-$C_3$ alkyl), —$NO_2$, and —C(=O)—(C1-$C_3$ alkyl).

25. The method of claim 24, wherein X is I.

26. The method of claim 23, wherein the alkyne is a compound having the formula:

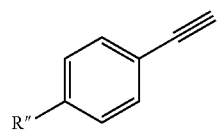

wherein R" is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl.

27. The method of claim 23, wherein the alkyne is a compound having the formula:

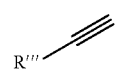

wherein R''' is selected from —H, $C_1$-$C_{10}$ alkyl, $C_3$-$C_6$ cycloalkyl, —O—($C_1$-$C_3$ alkyl), aryl, ($C_1$-$C_3$ alkyl)-($C_3$-$C_6$ cycloalkyl), and ($C_1$-$C_3$ alkyl)-aryl.

28. The method of claim 23, wherein the alkynone is a compound having the formula:

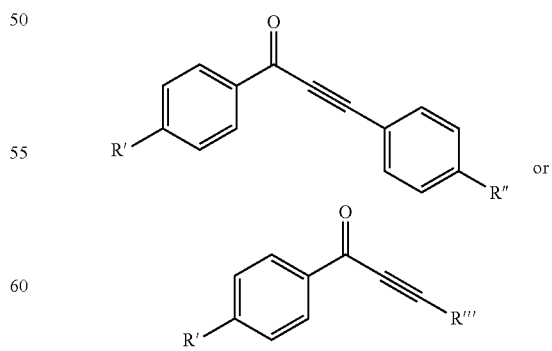

or a pharmaceutically acceptable salt thereof.

29. The method of claim 23, wherein the compound of Formula (I) is selected from:

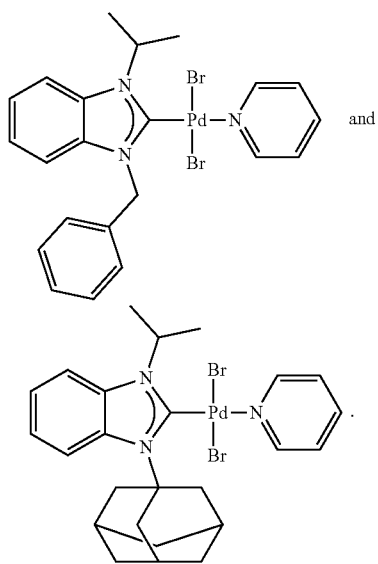
30. The method of claim 23, wherein the compound of Formula (I) is present in an amount of about 0.01 mol % to about 1.0 mol %.
* * * * *